(12) United States Patent
Koike

(10) Patent No.: US 7,448,487 B2
(45) Date of Patent: Nov. 11, 2008

(54) TRANSPORTING APPARATUS

(75) Inventor: Hiroki Koike, Kobe (JP)

(73) Assignee: Sysmex Corporation, Kobe (JP)

( * ) Notice: Subject to any disclaimer, the term of this patent is extended or adjusted under 35 U.S.C. 154(b) by 131 days.

(21) Appl. No.: 11/389,070

(22) Filed: Mar. 27, 2006

(65) Prior Publication Data

US 2006/0216198 A1 Sep. 28, 2006

(30) Foreign Application Priority Data

Mar. 28, 2005 (JP) ............................. 2005-091135

(51) Int. Cl.
*B65G 43/08* (2006.01)
(52) U.S. Cl. .................... 198/358; 198/349; 198/867.11
(58) Field of Classification Search ............ 198/867.11, 198/867.12, 803.14, 803.15, 803.11, 349, 198/358, 349.1, 349.5, 349.6
See application file for complete search history.

(56) References Cited

U.S. PATENT DOCUMENTS 5,529,166 A * 6/1996 Markin et al. ............... 198/349
6,274,092 B1 * 8/2001 Itoh ........................... 422/104
6,343,690 B1 * 2/2002 Britton et al. ............ 198/803.6
6,520,313 B1 * 2/2003 Kaarakainen et al. ....... 198/358
6,971,506 B2 * 12/2005 Hassinen et al. ........ 198/803.14

FOREIGN PATENT DOCUMENTS

JP 63-141455 U 9/1988

* cited by examiner

*Primary Examiner*—James R Bidwell
(74) *Attorney, Agent, or Firm*—Birch, Stewart, Kolasch & Birch, LLP

(57) ABSTRACT

A transporting apparatus is described, a representative one of which includes a transporting apparatus which transports at least one specimen container accommodated in a rack to a specimen supplying position for supplying a specimen processing apparatus, comprising: a transport mechanism configured to transport the at least one specimen container to the specimen supplying position by transporting the rack; and a detection unit for obtaining information specifying the position of the rack being transported by the transport mechanism.

20 Claims, 28 Drawing Sheets

[Fig. 1]
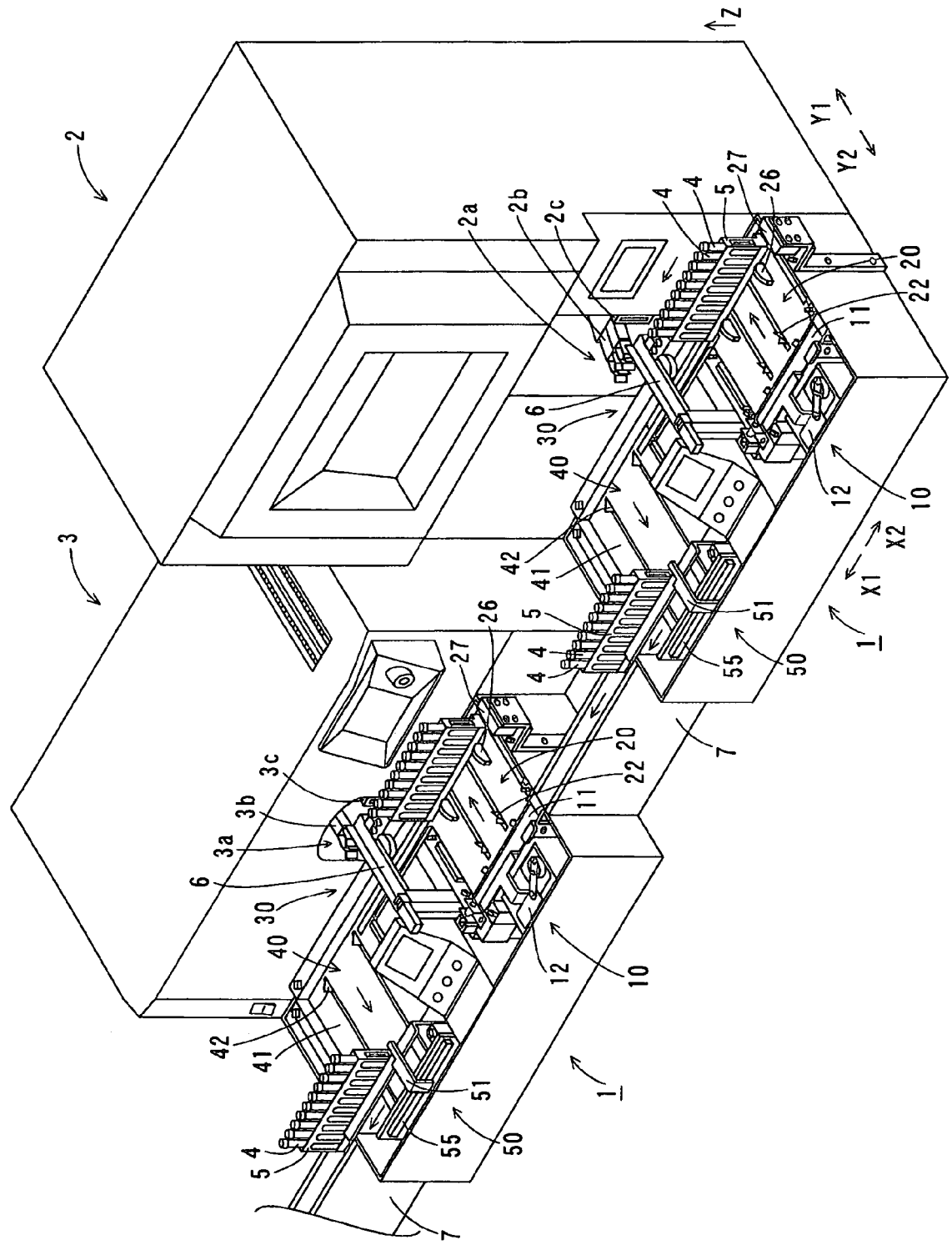

[Fig. 2]
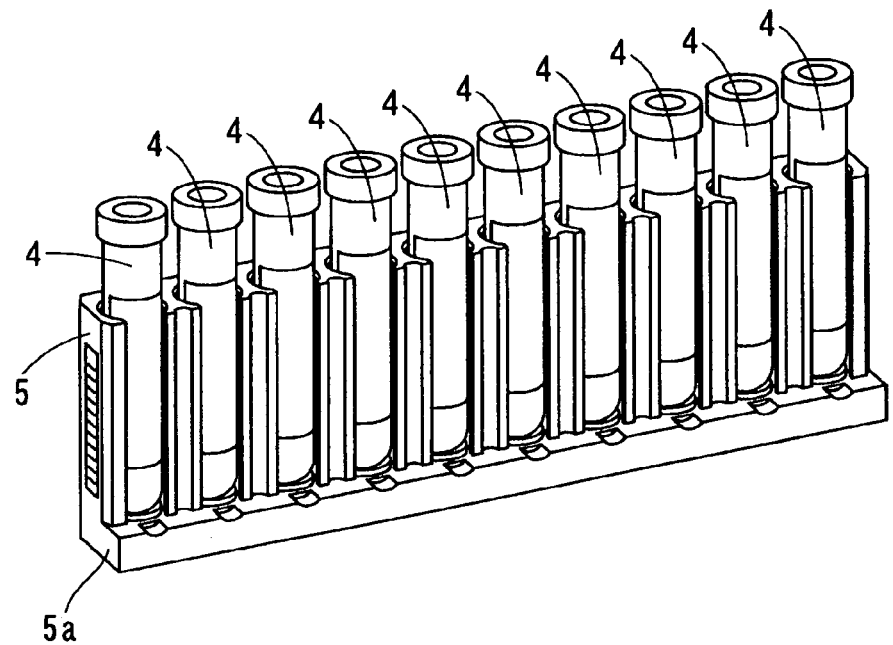
[Fig. 3]
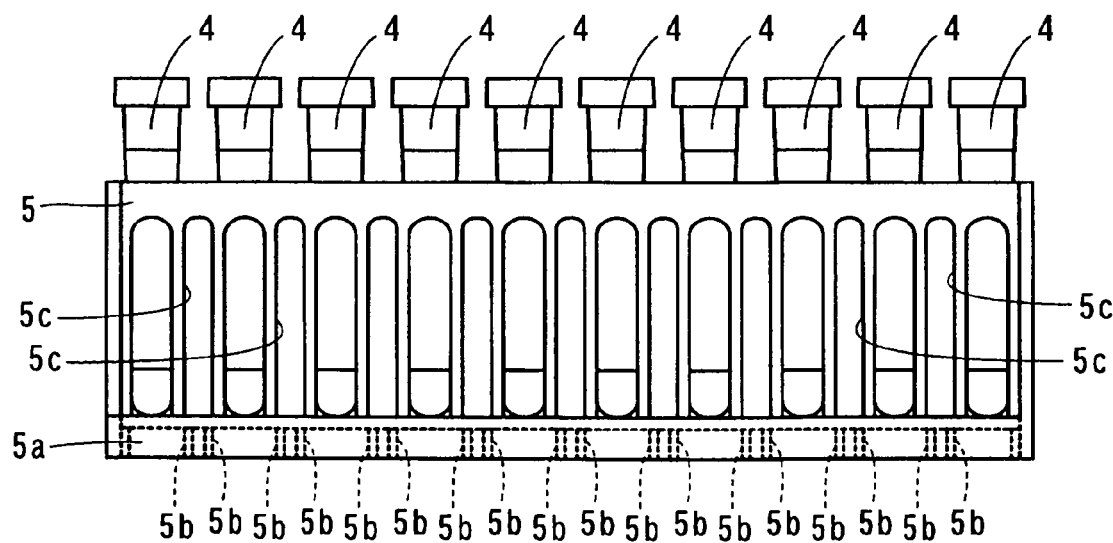

[Fig. 4]
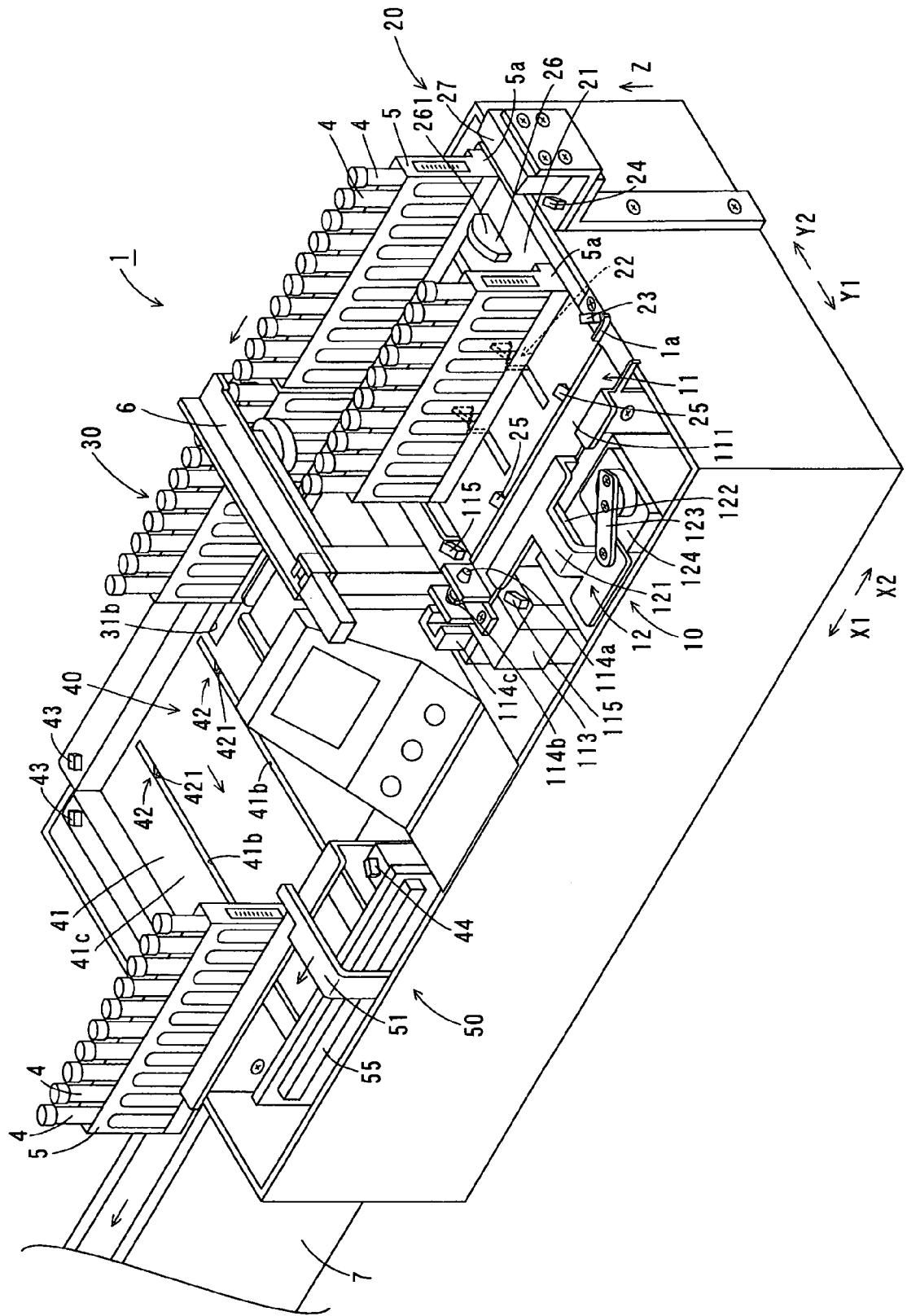

[Fig. 5]
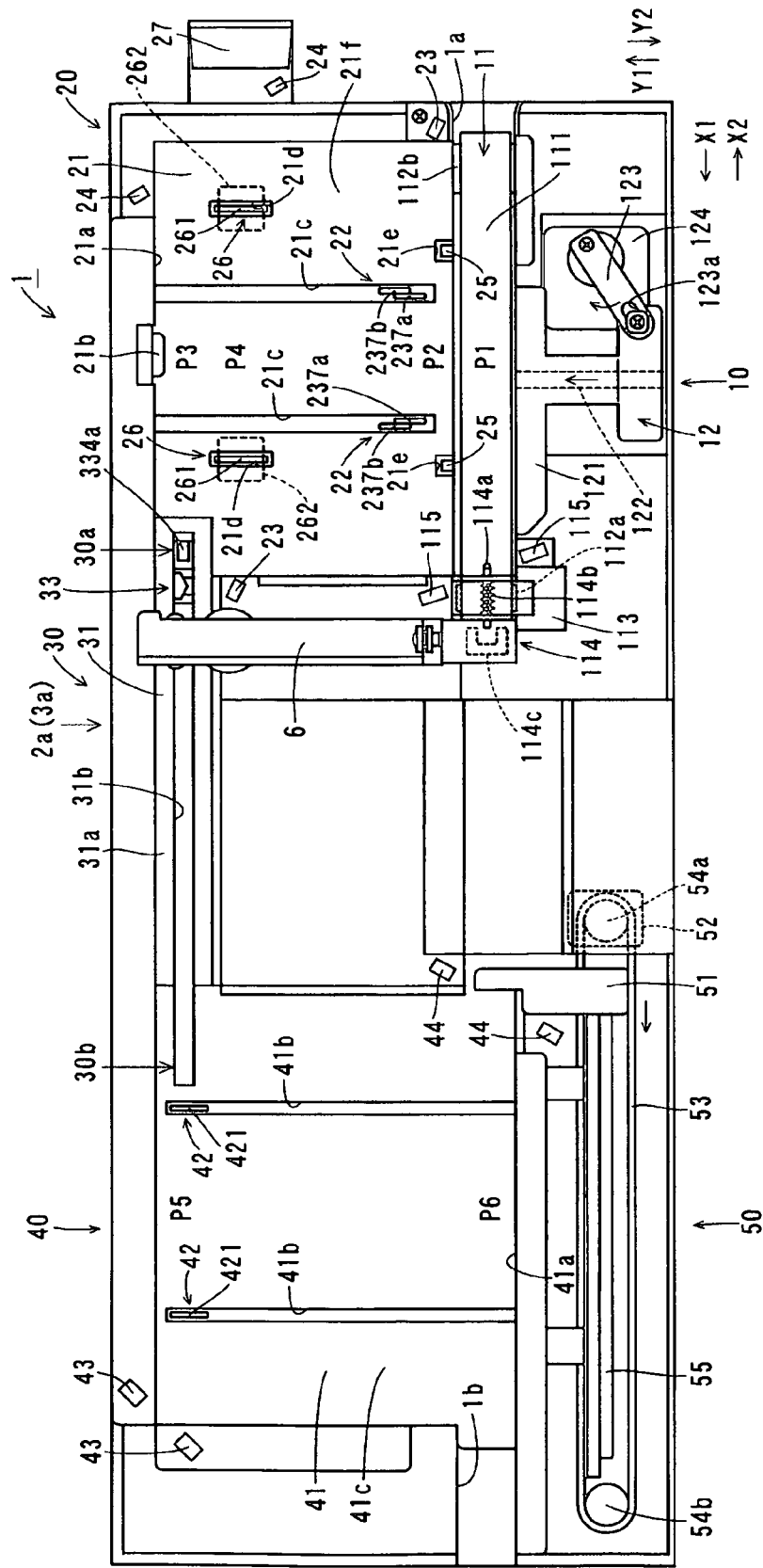

[Fig. 6]
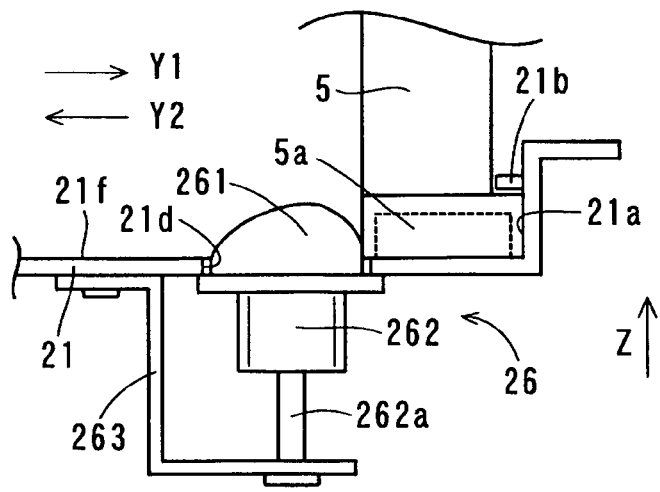
[Fig. 7]
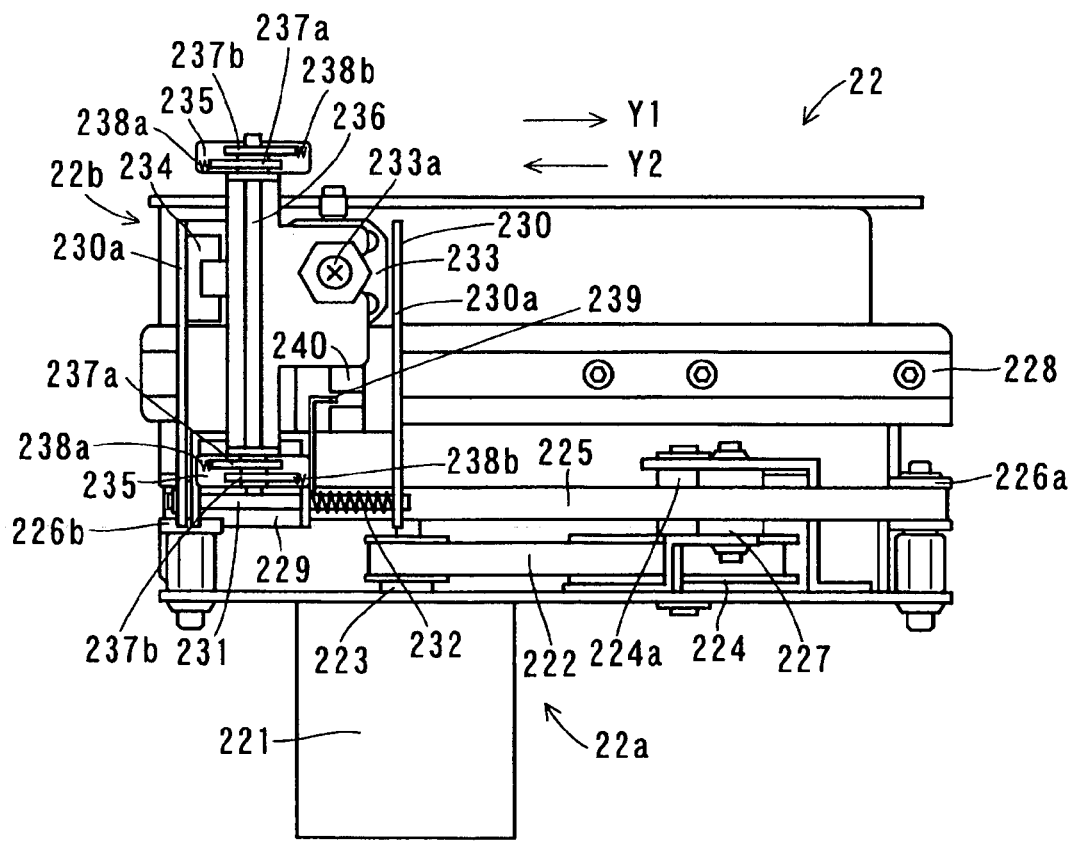

[Fig. 8]
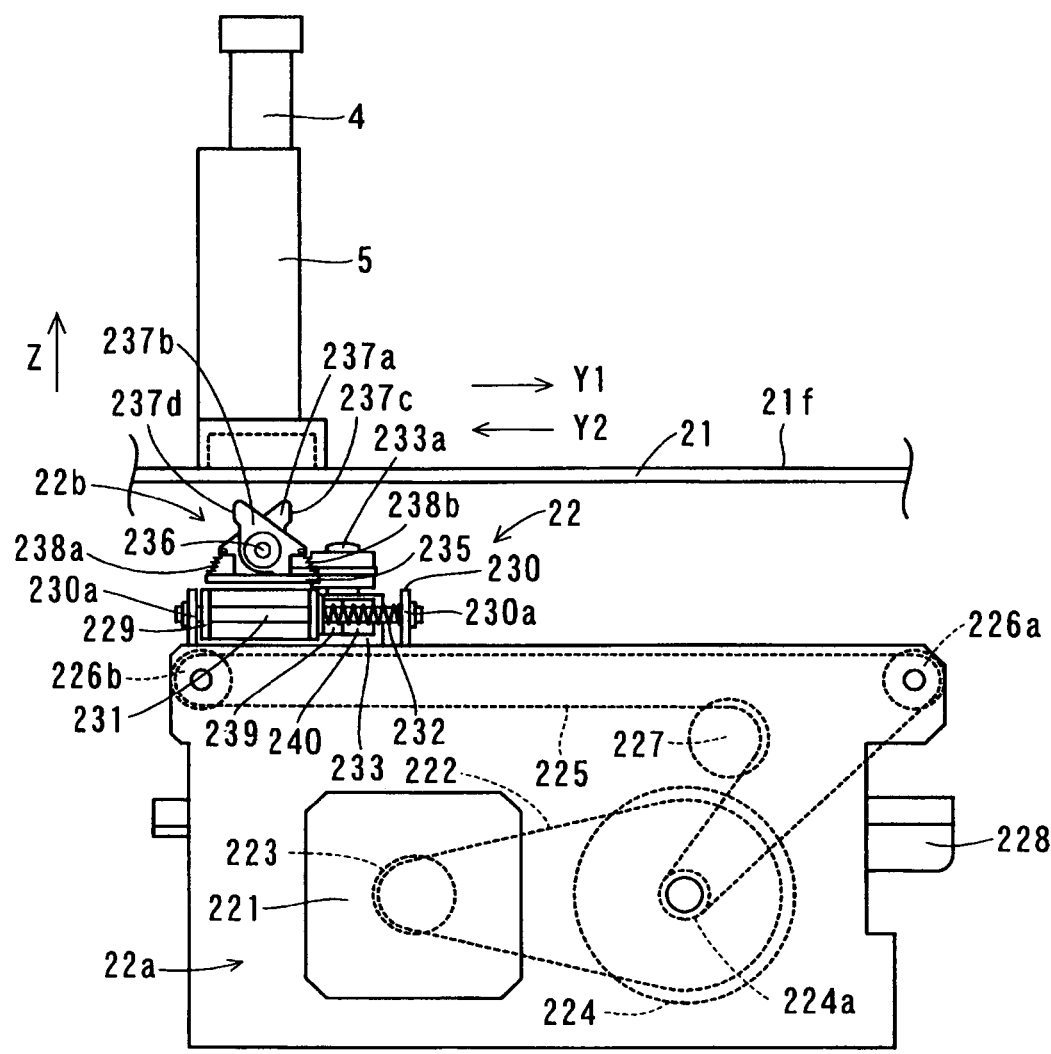

[Fig. 9]
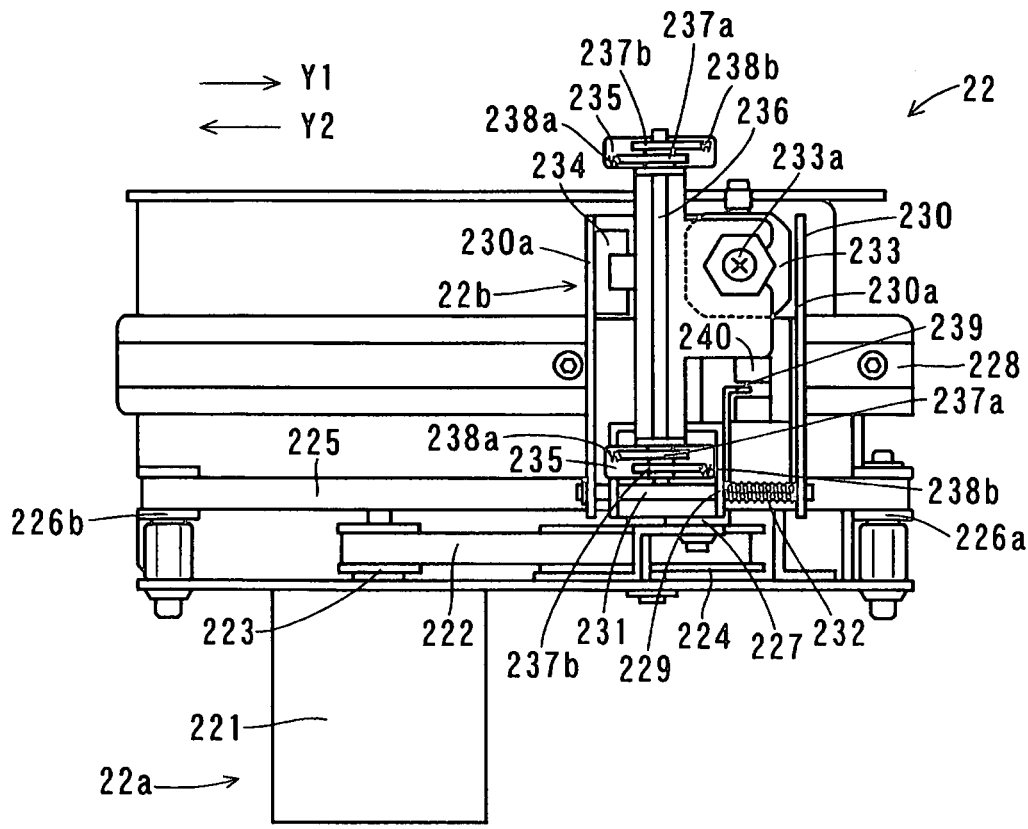
[Fig. 10]
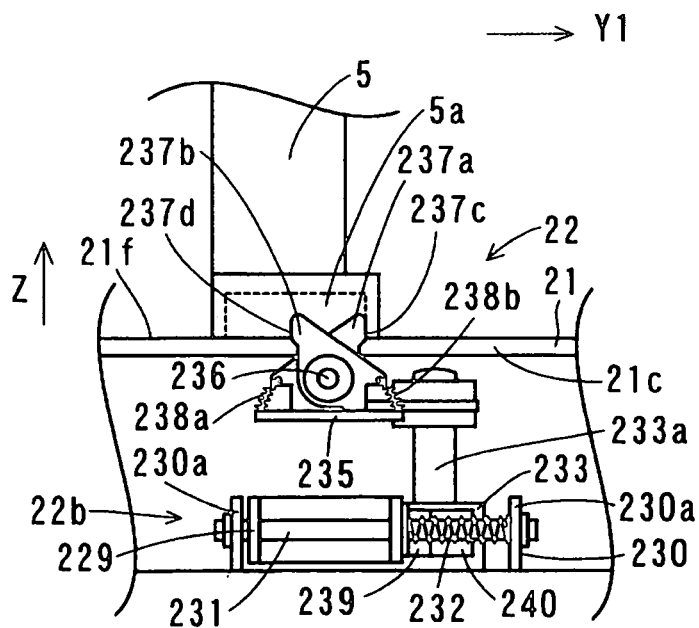

[Fig. 11]
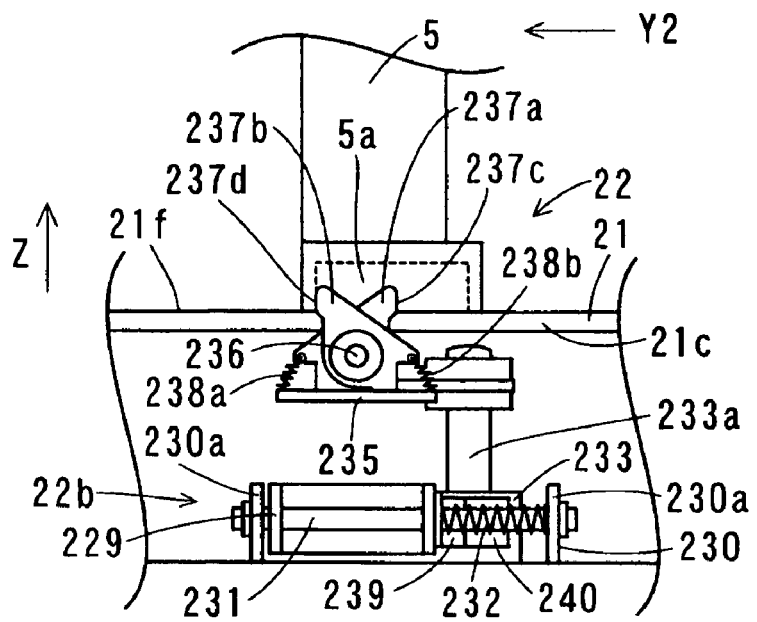
[Fig. 12]
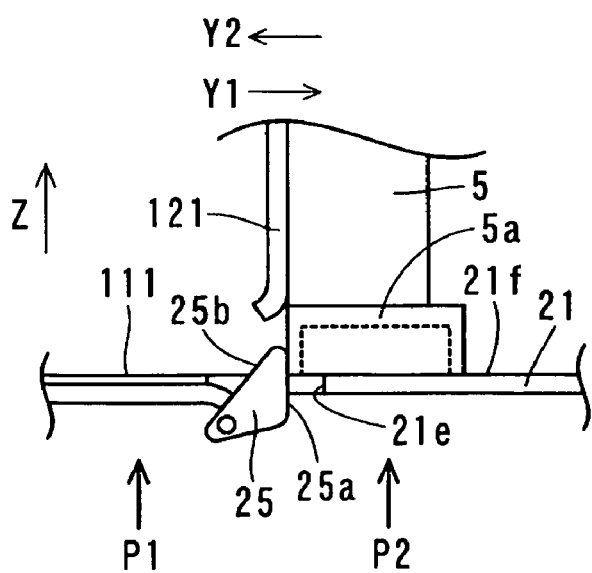

[Fig. 13]
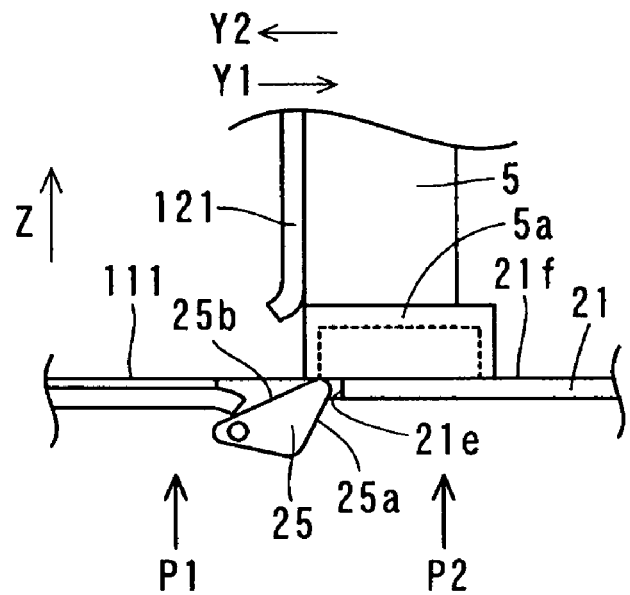
[Fig. 14]
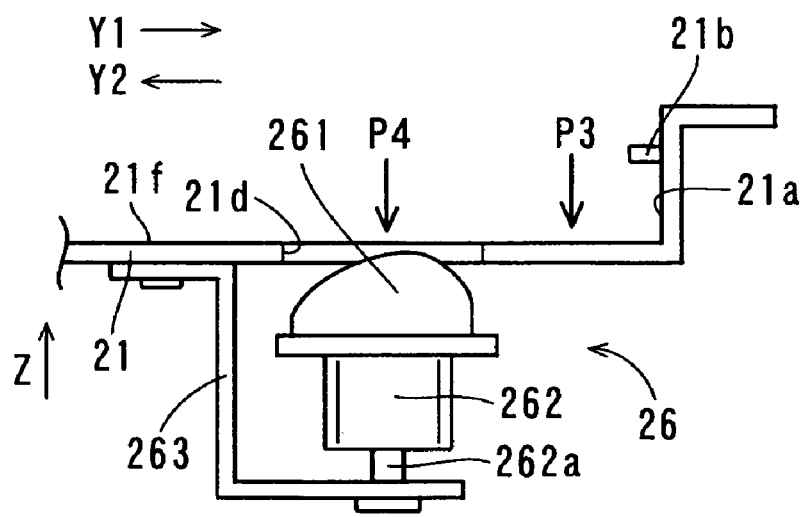

[Fig. 15]
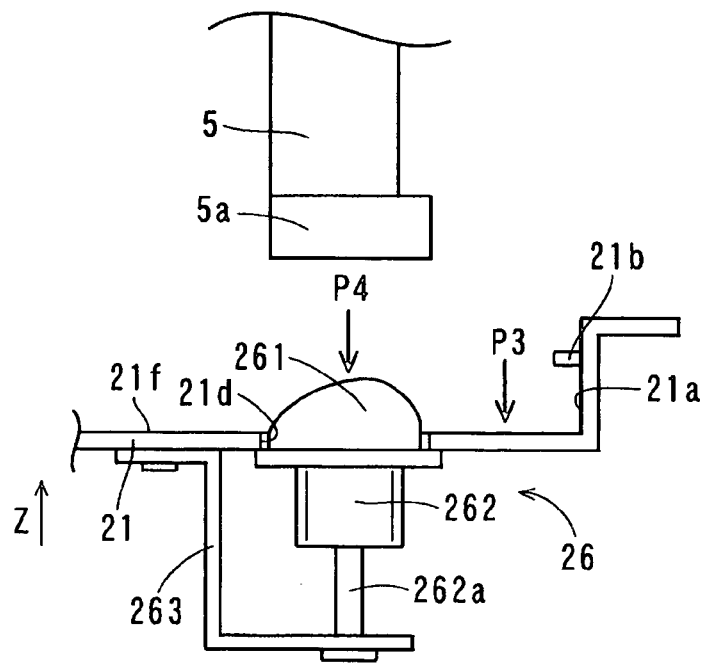
[Fig. 16]
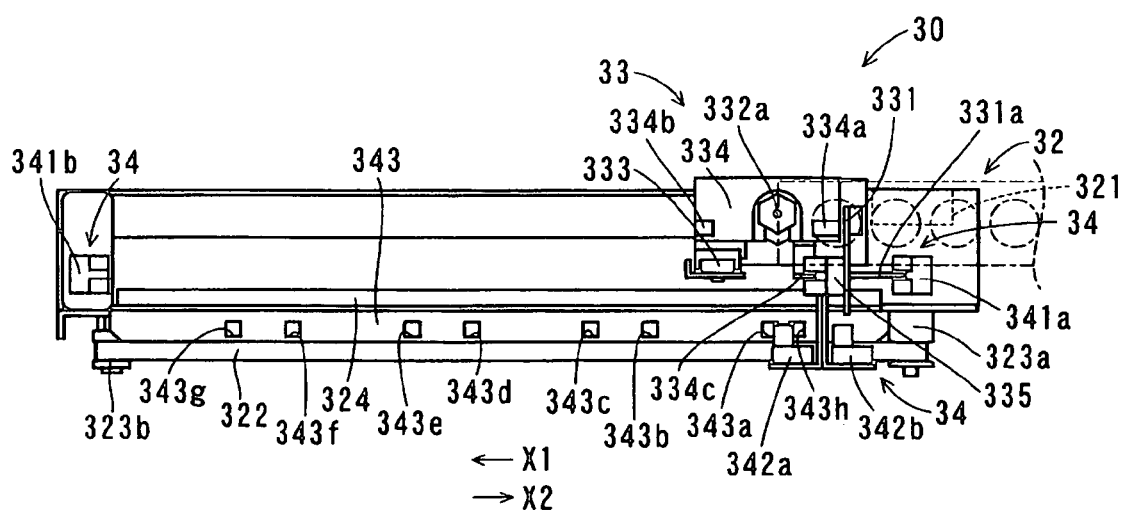

[Fig. 17]
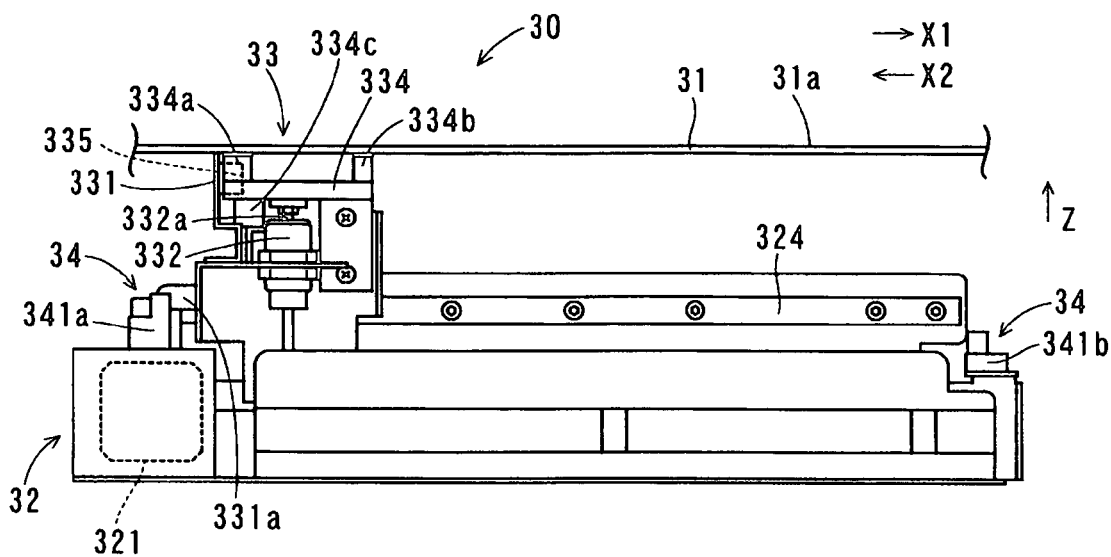
[Fig. 18]
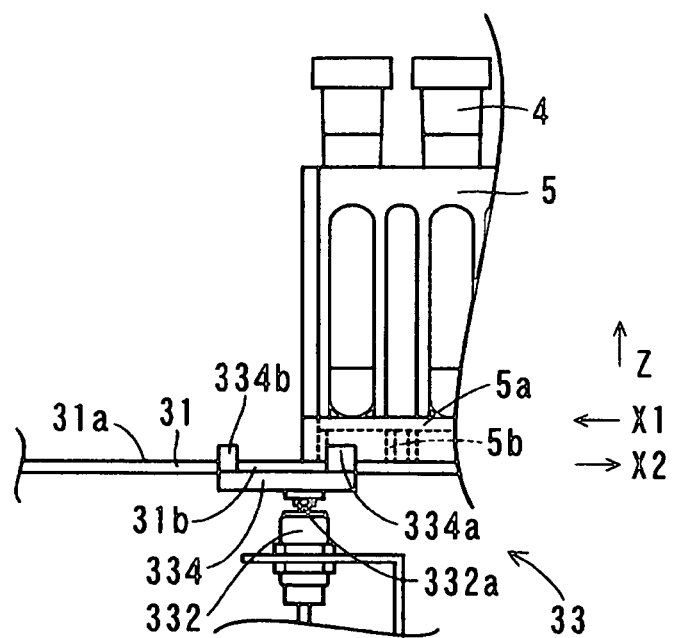

[Fig. 19]
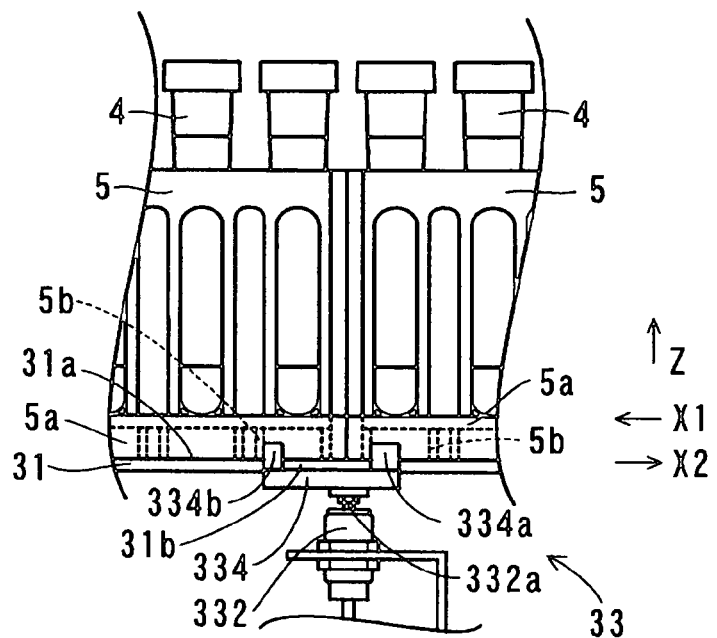
[Fig. 20]
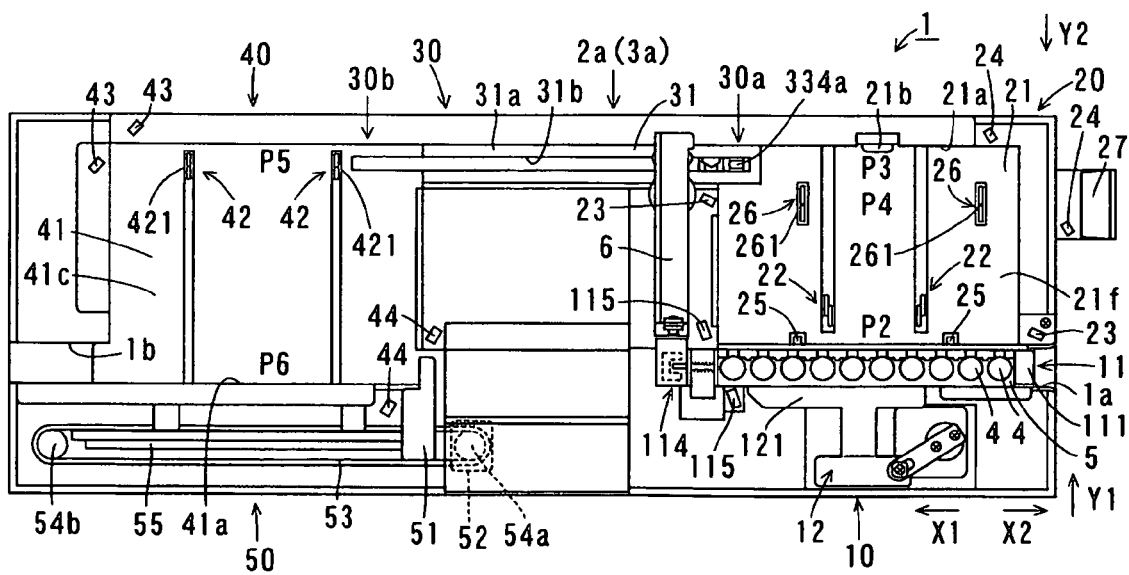

[Fig. 21]
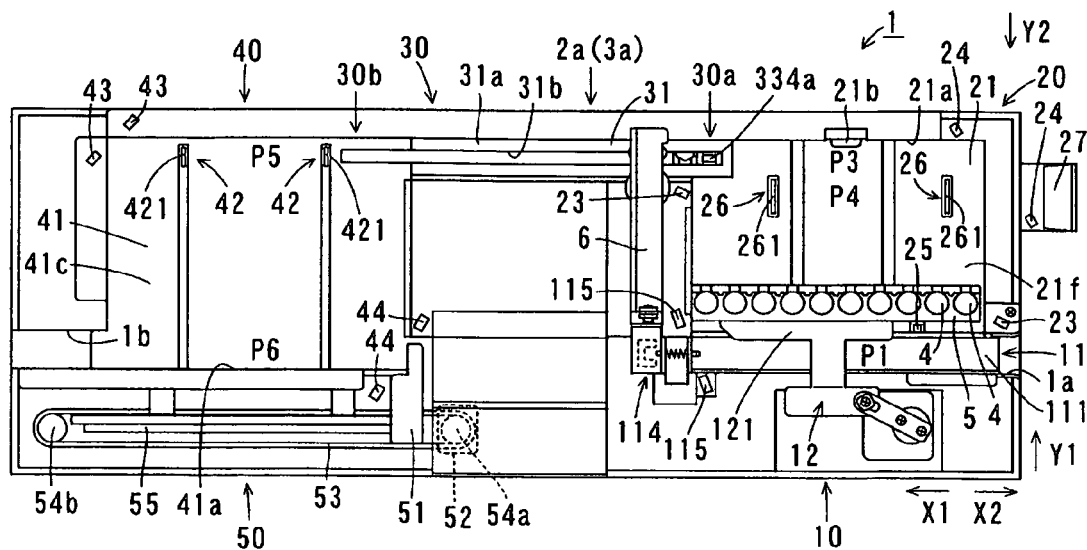
[Fig. 22]
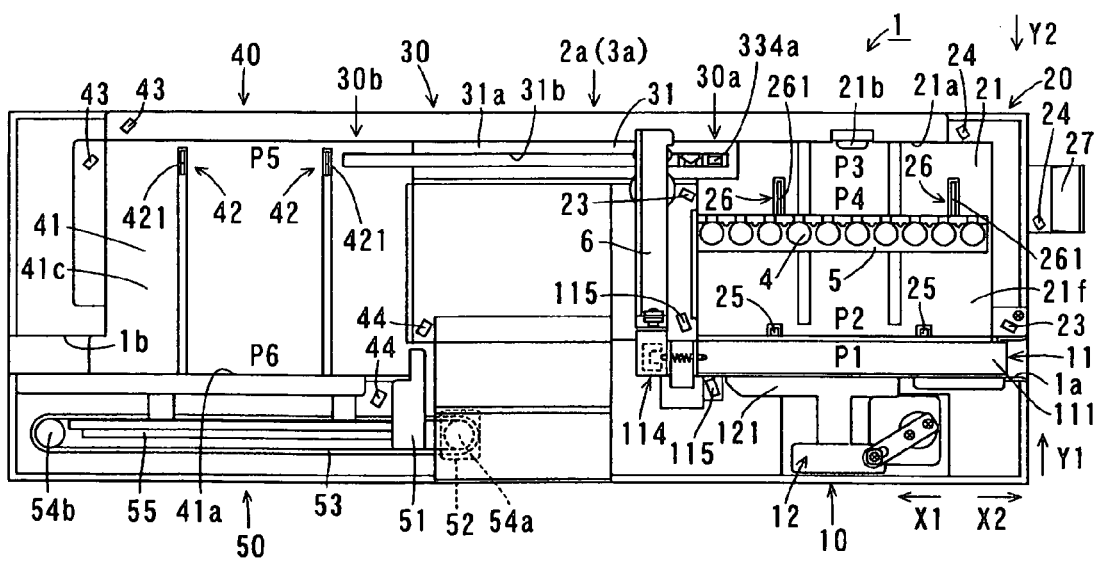

[Fig. 23]
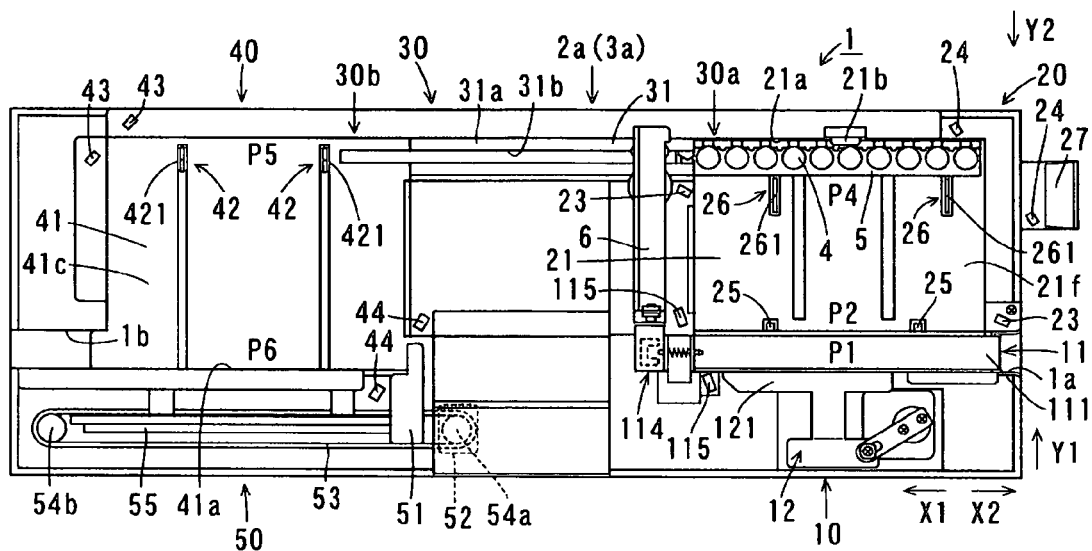
[Fig. 24]
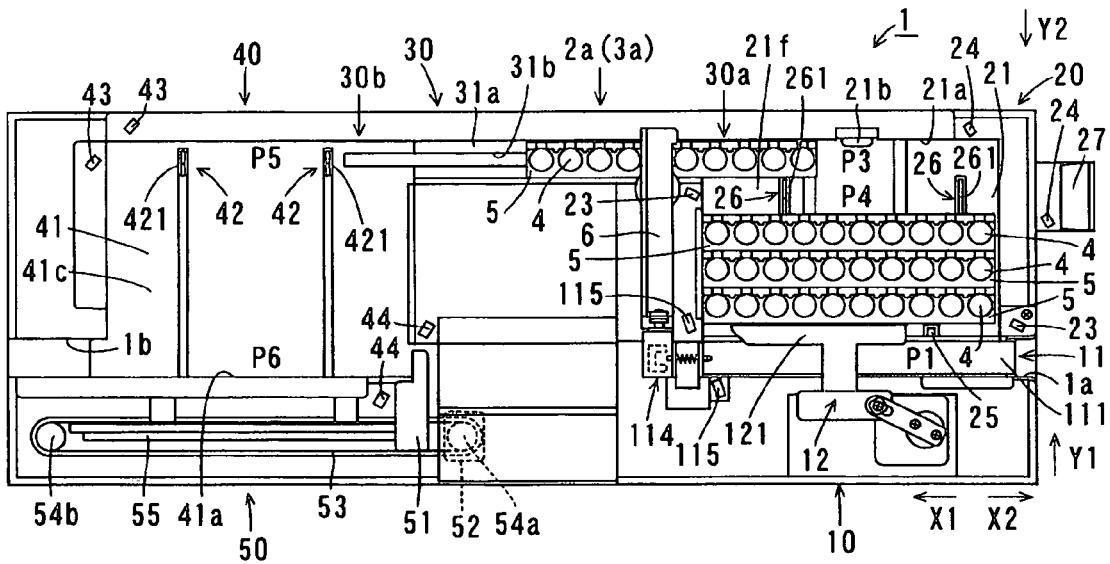

[Fig. 25]
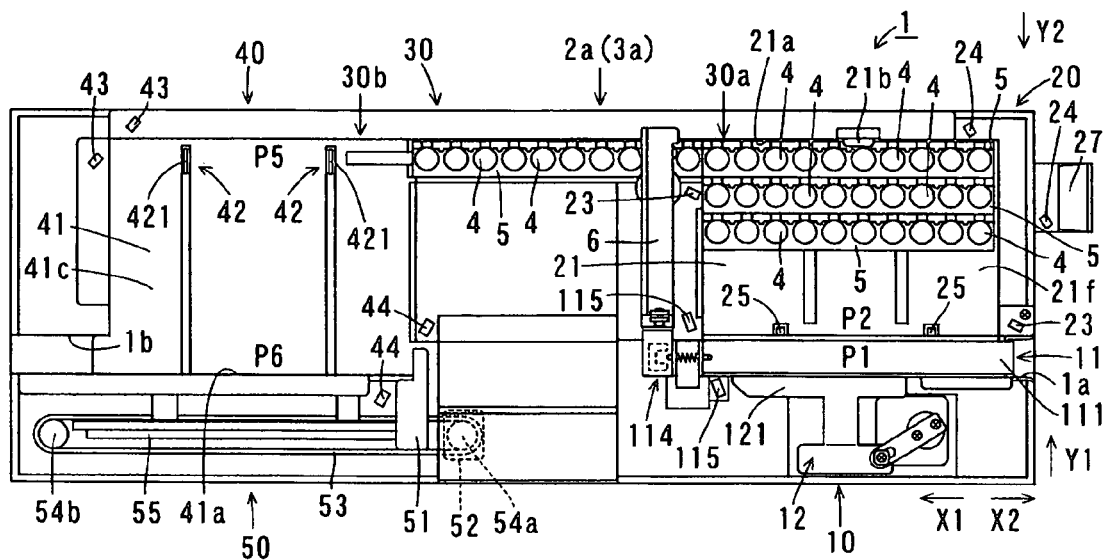
[Fig. 26]
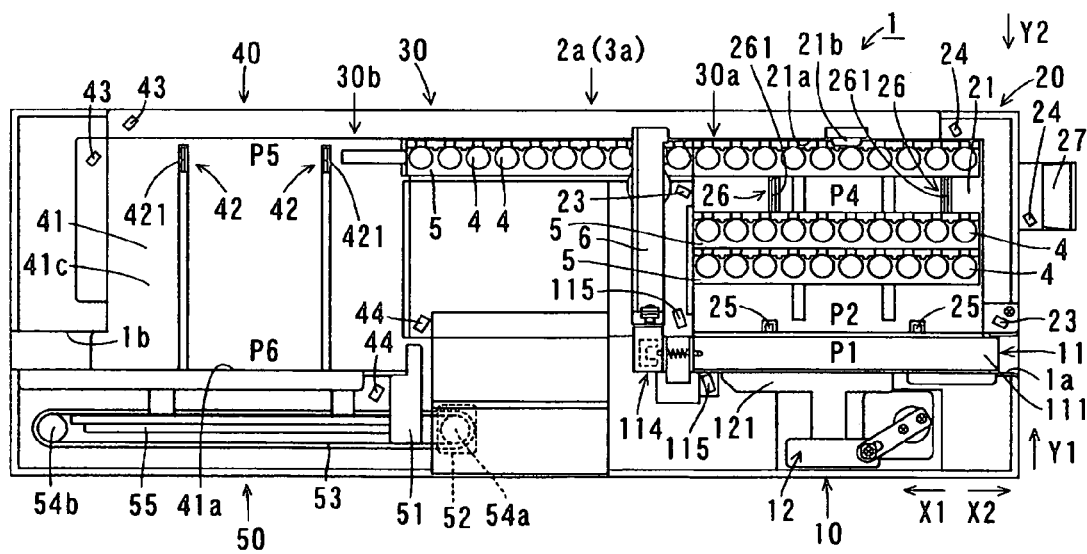

[Fig. 27]
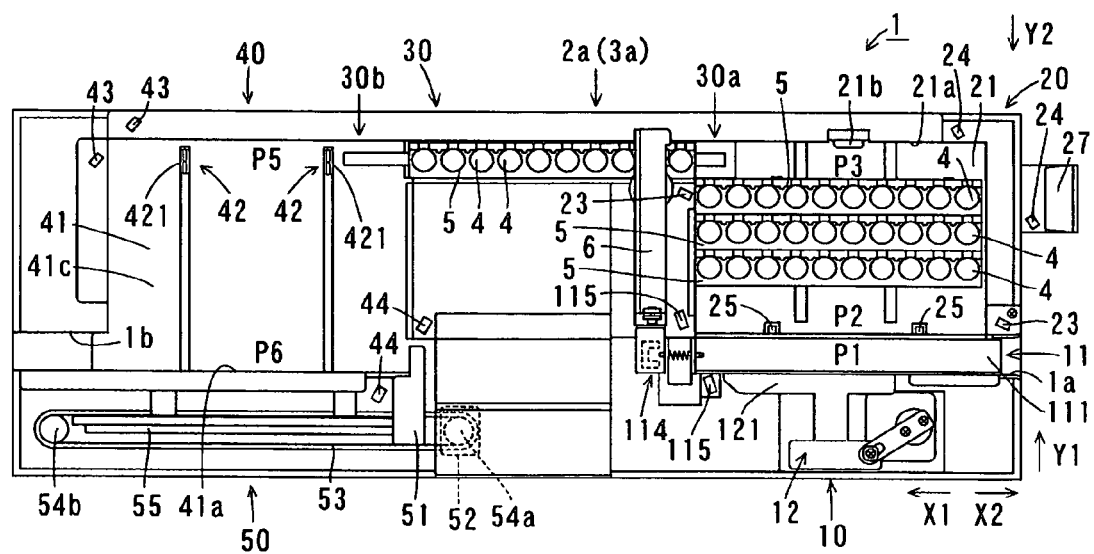
[Fig. 28]
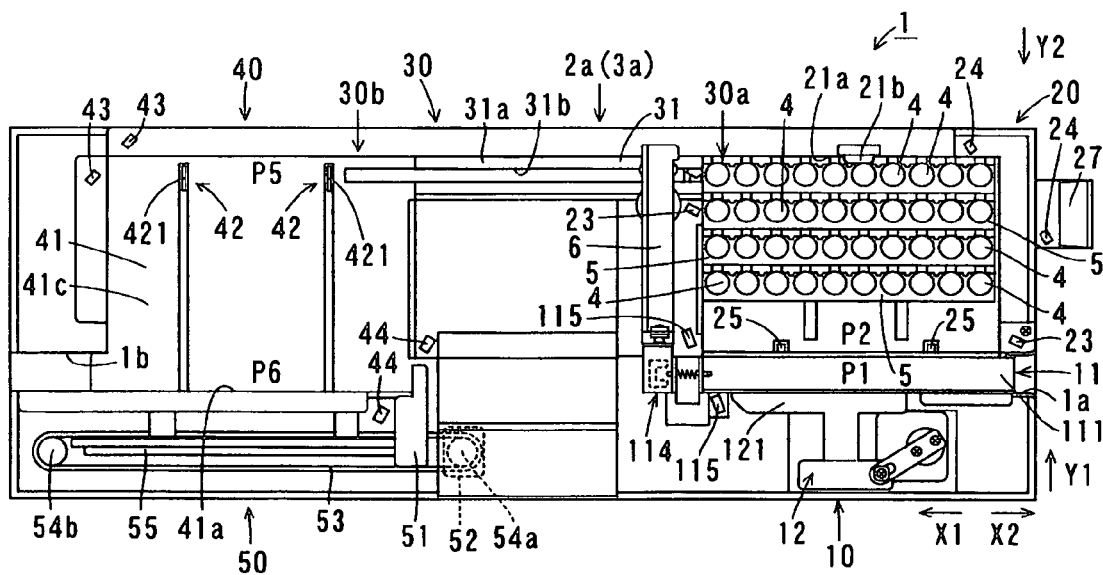

[Fig. 29]
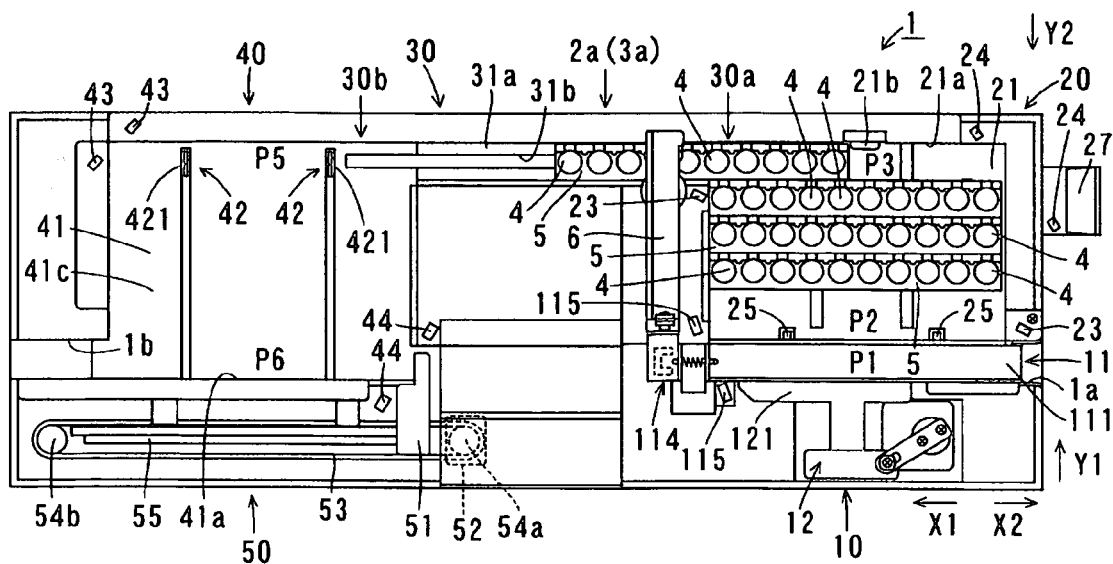
[Fig. 30]
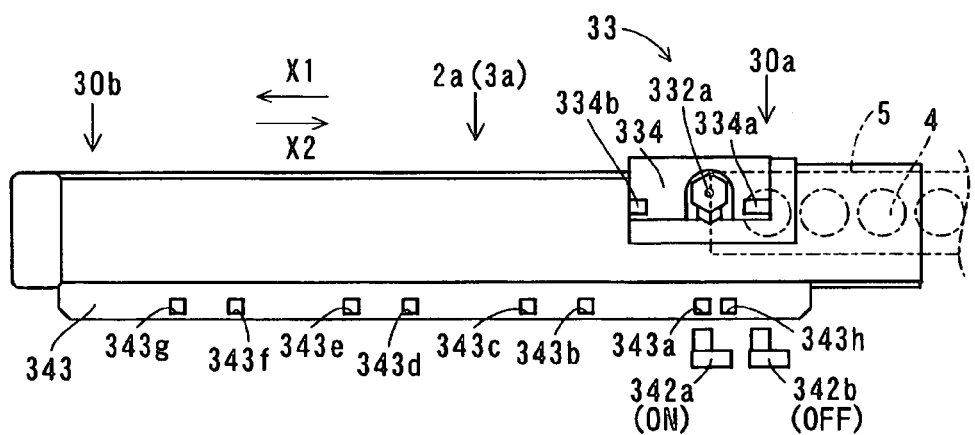

[Fig. 31]
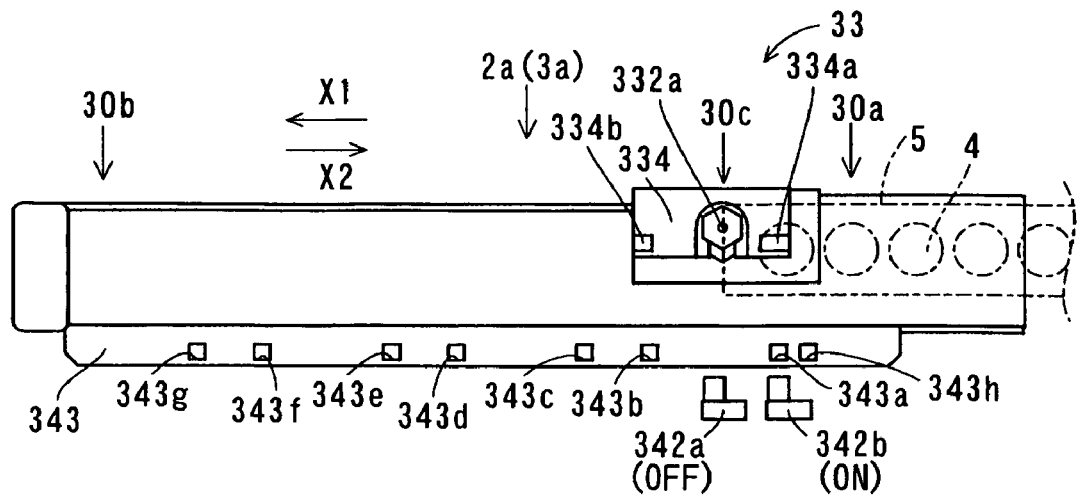
[Fig. 32]
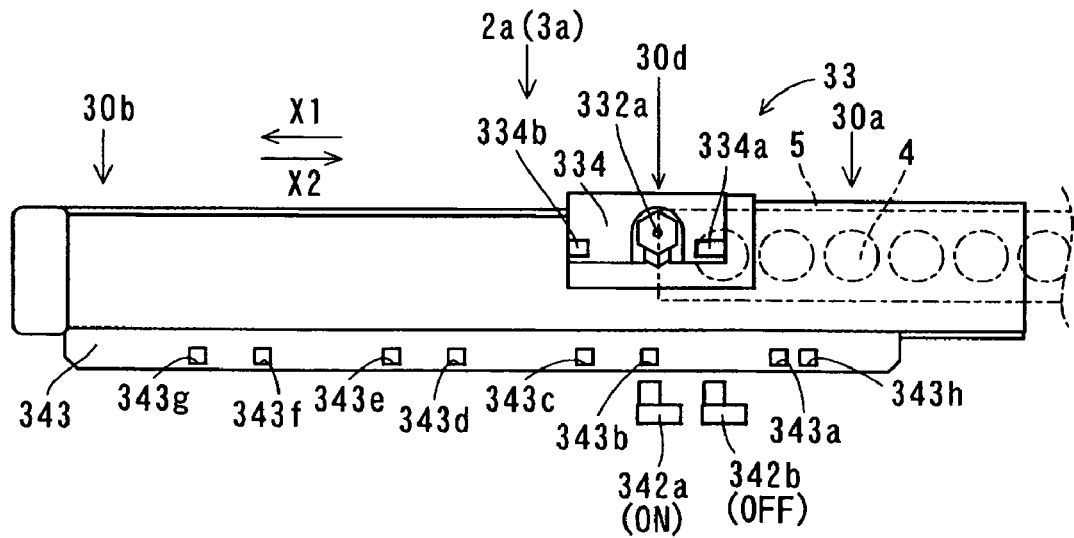

[Fig. 33]
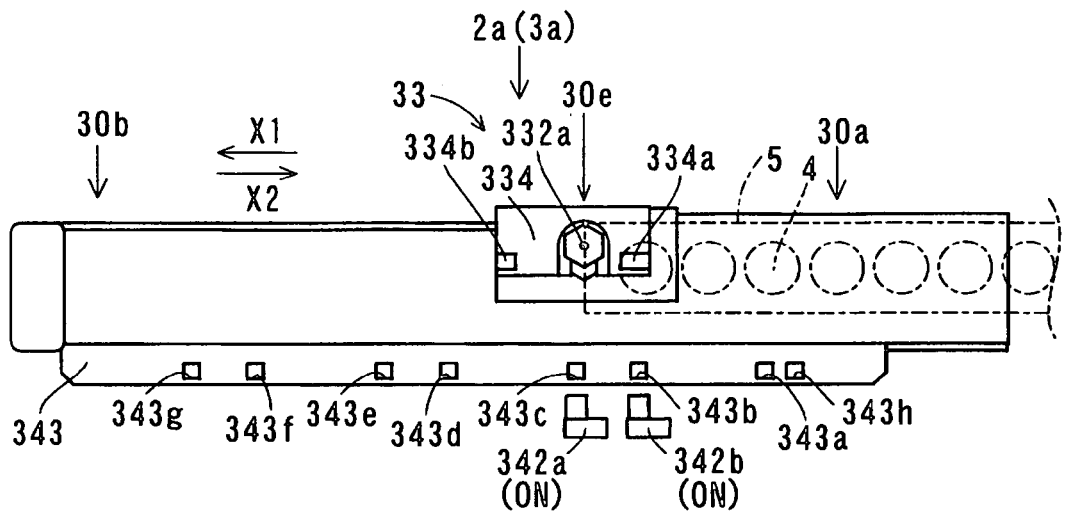
[Fig. 34]
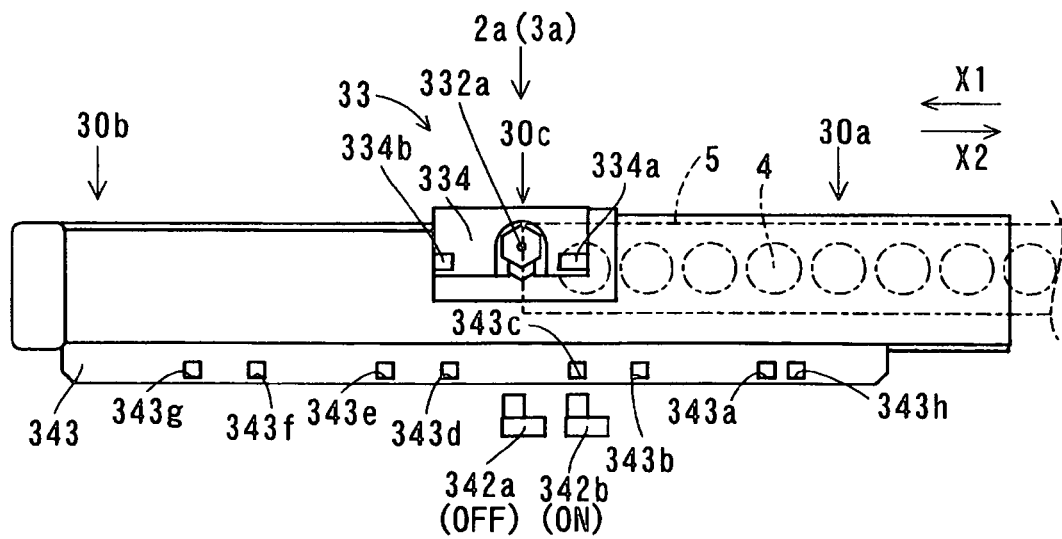

[Fig. 35]
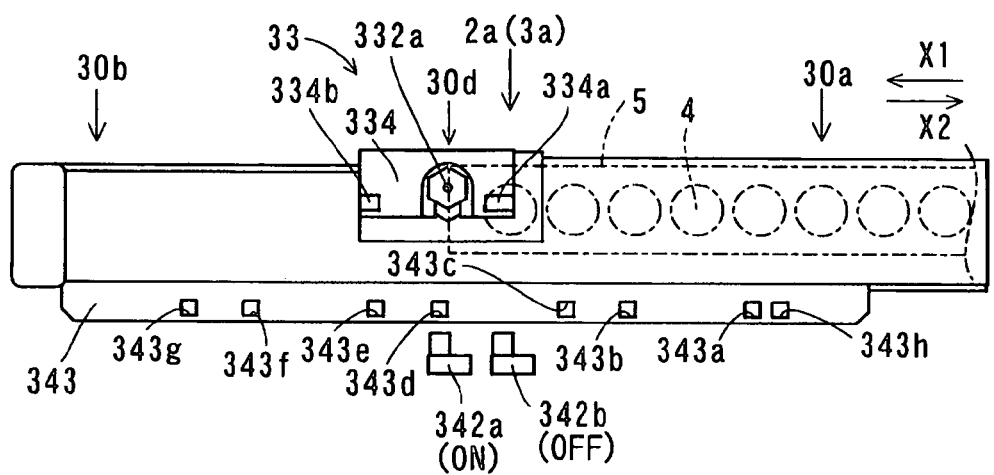
[Fig. 36]
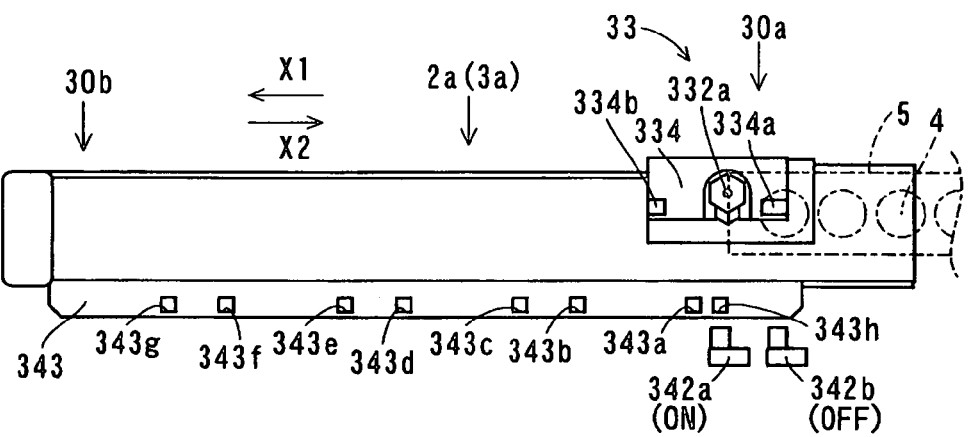

[Fig. 37]
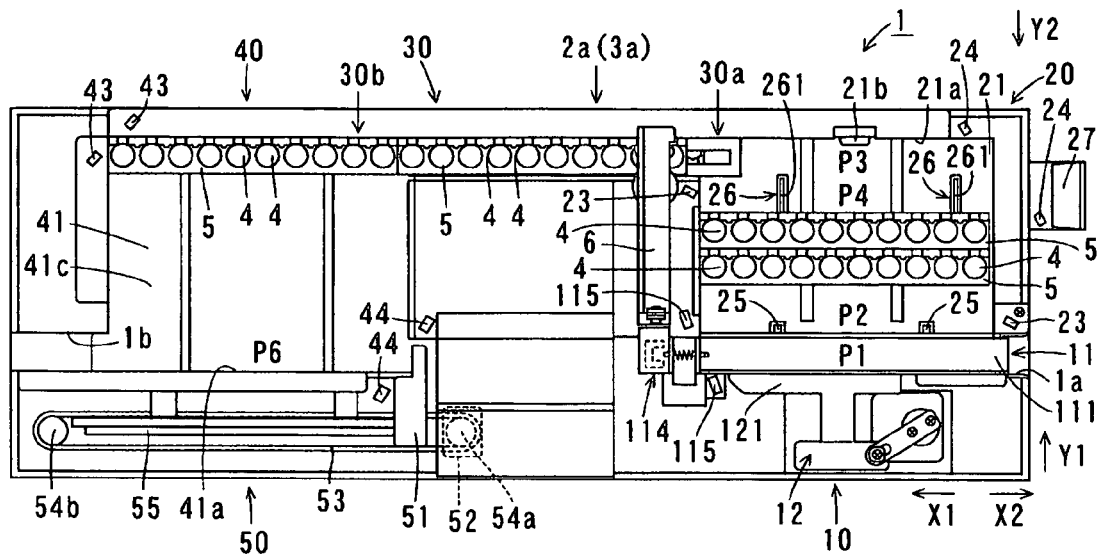
[Fig. 38]
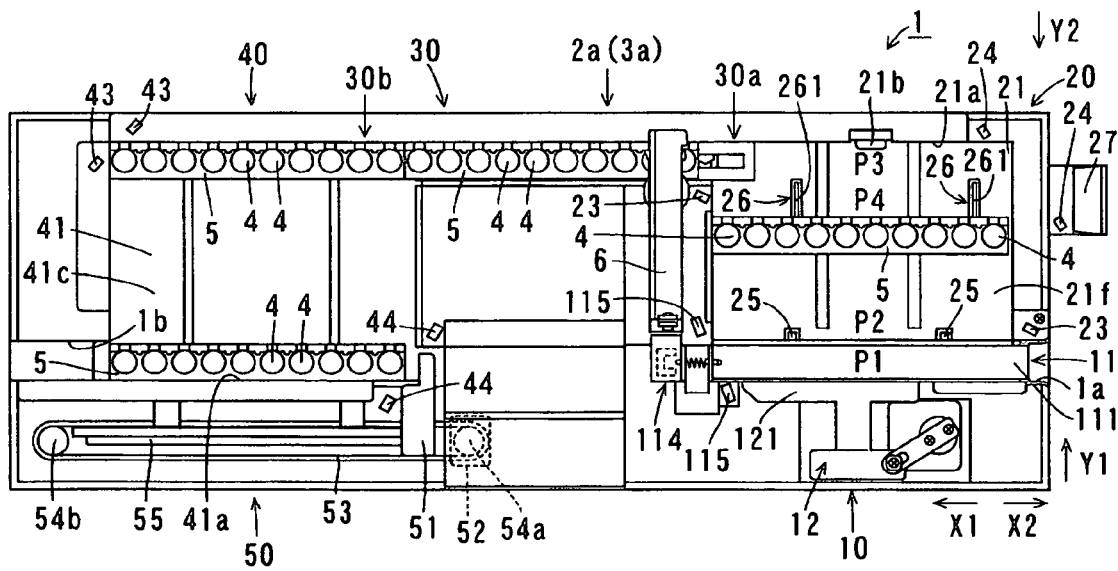

[Fig. 39]
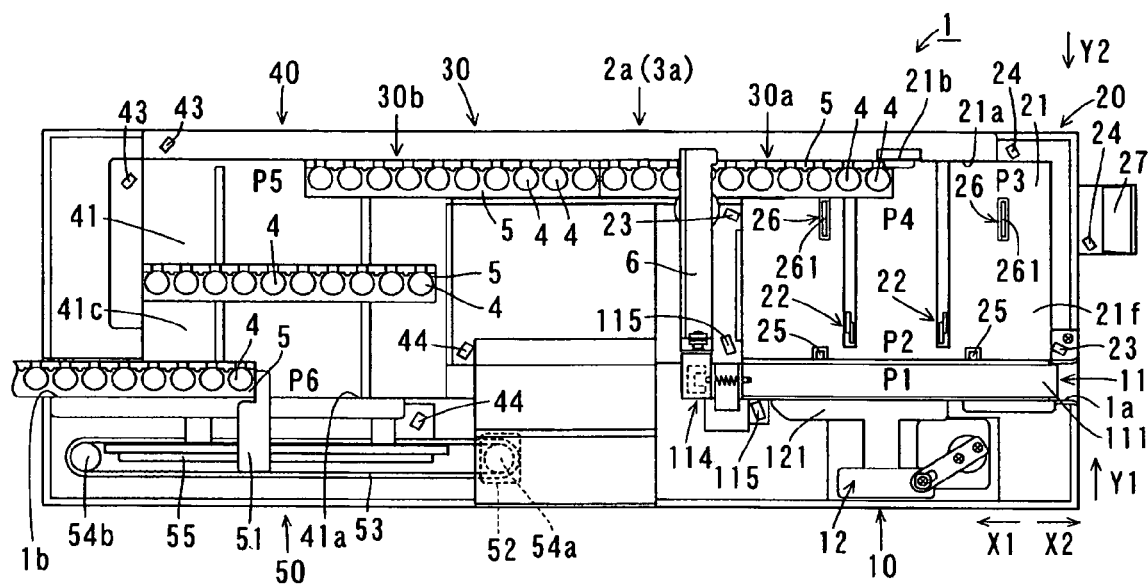

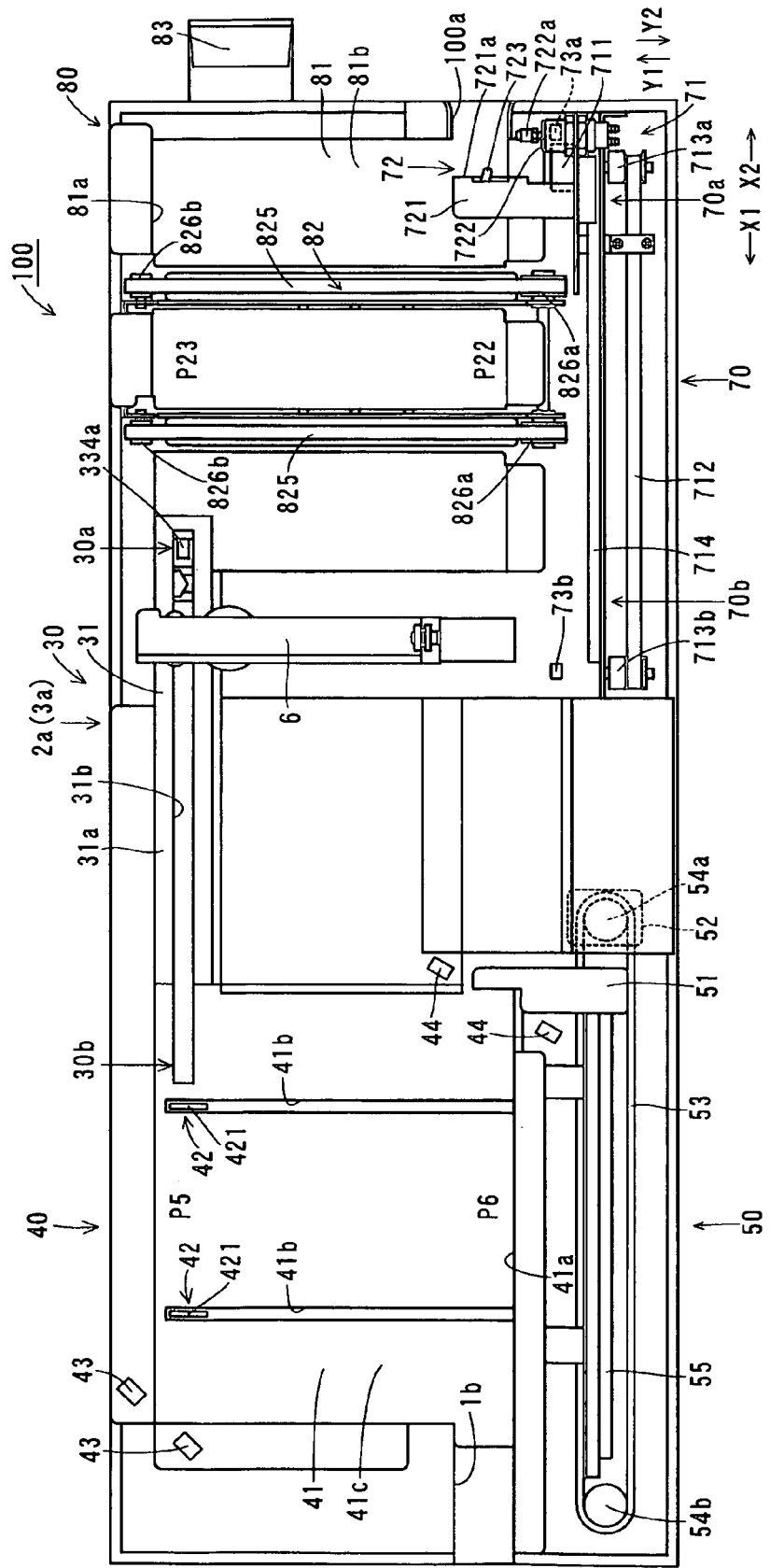
[Fig. 40]

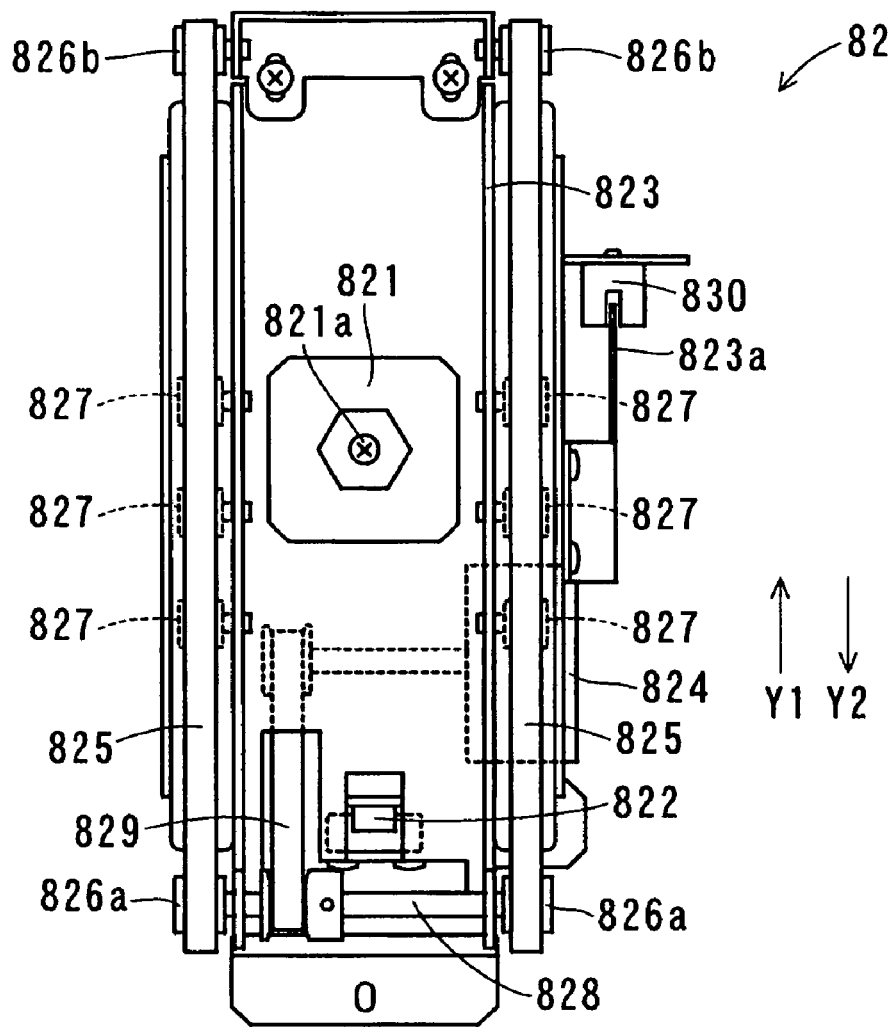
[Fig. 41]

[Fig. 42]
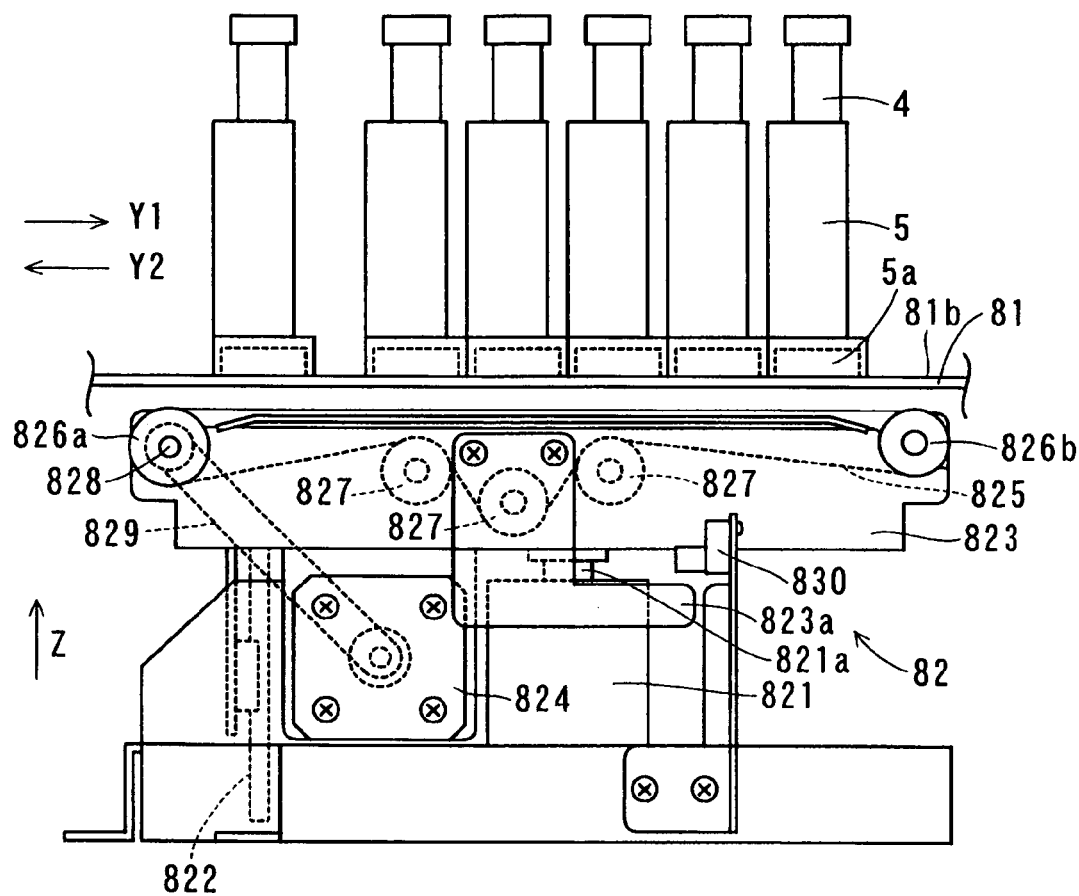

[Fig. 43]
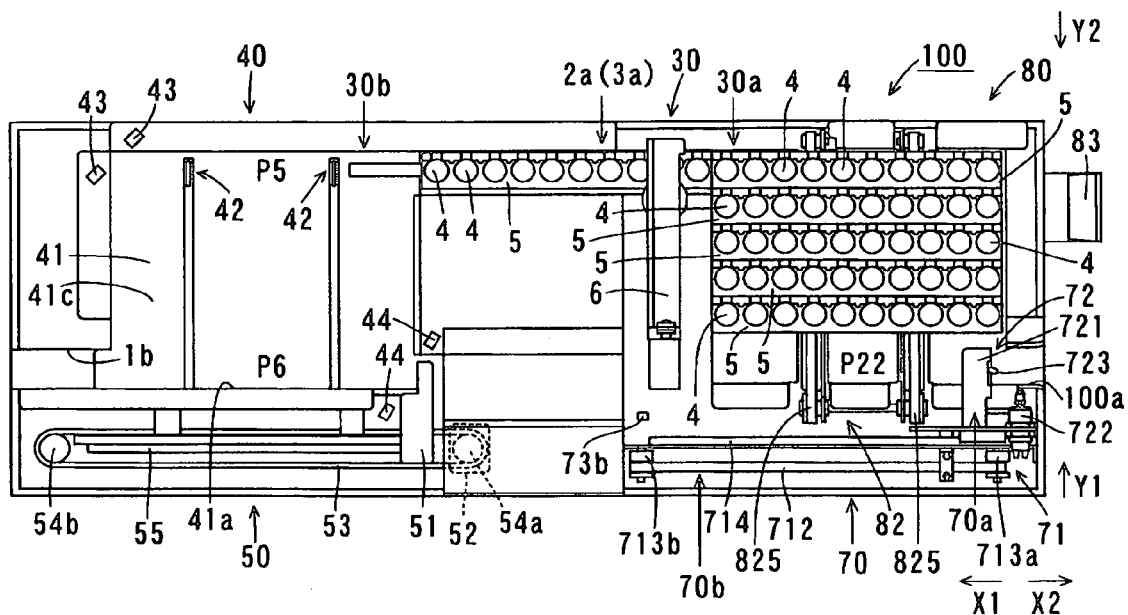
[Fig. 44]
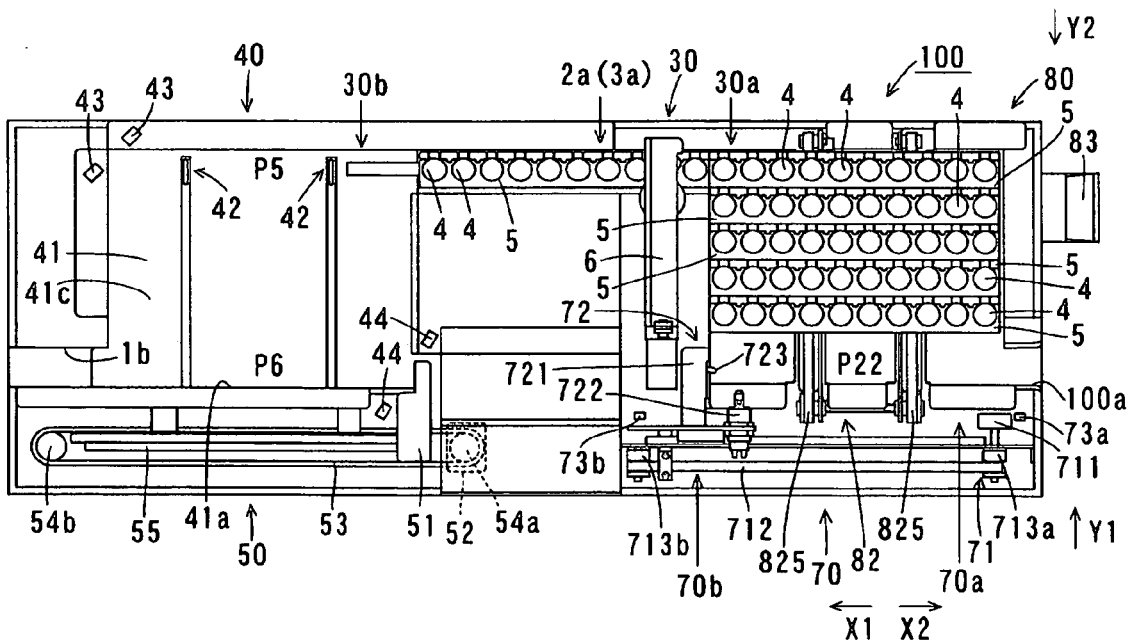

[Fig. 45]
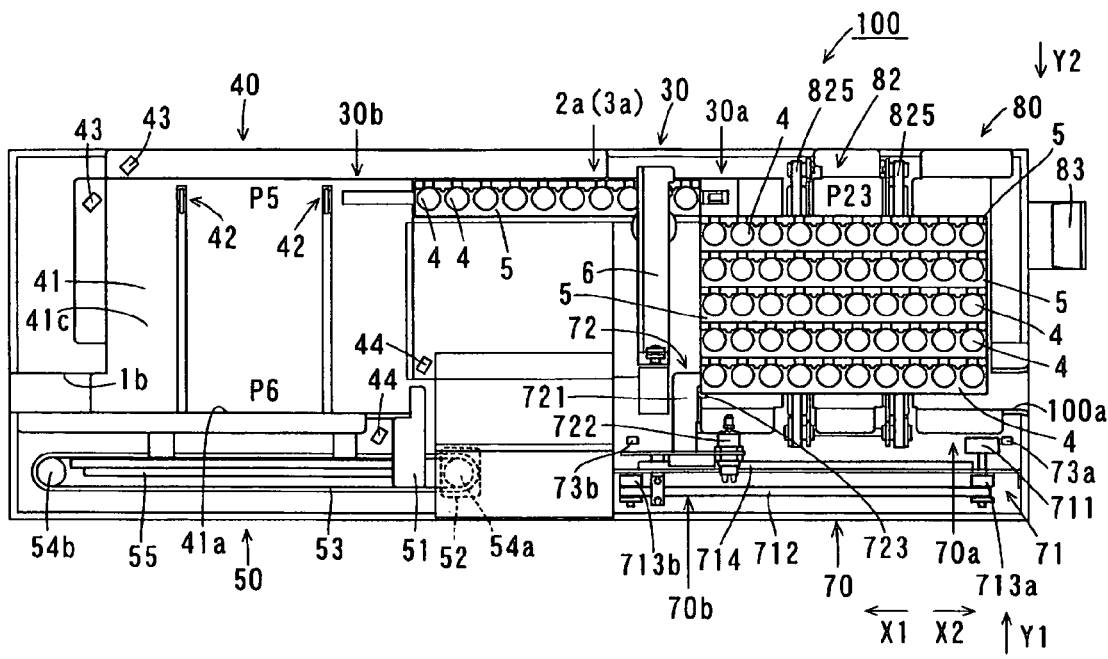
[Fig. 46]
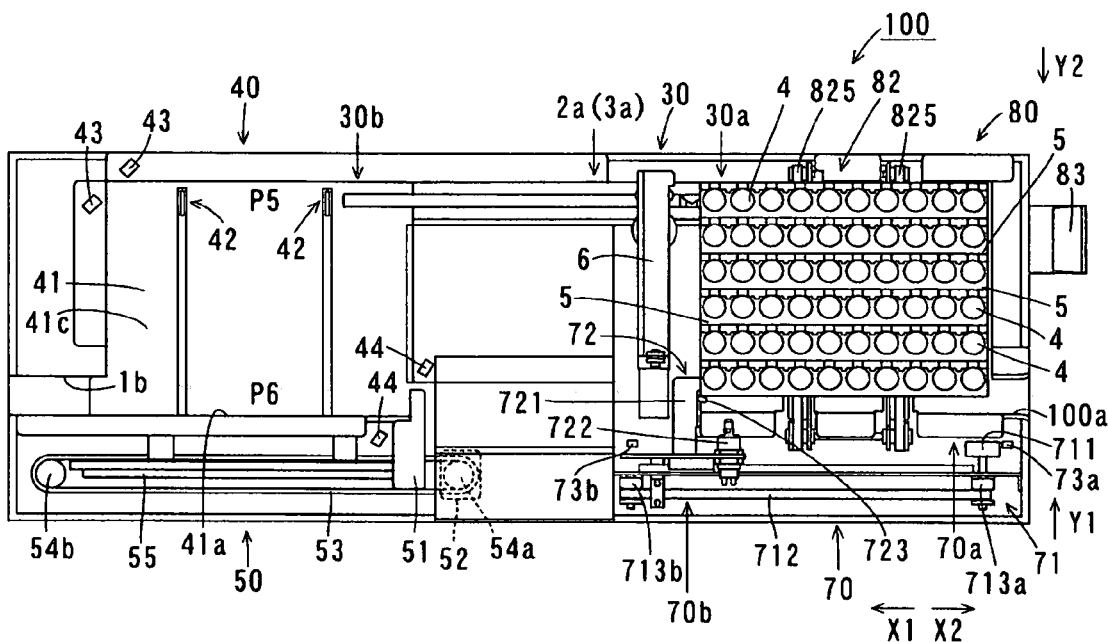

[Fig. 47]
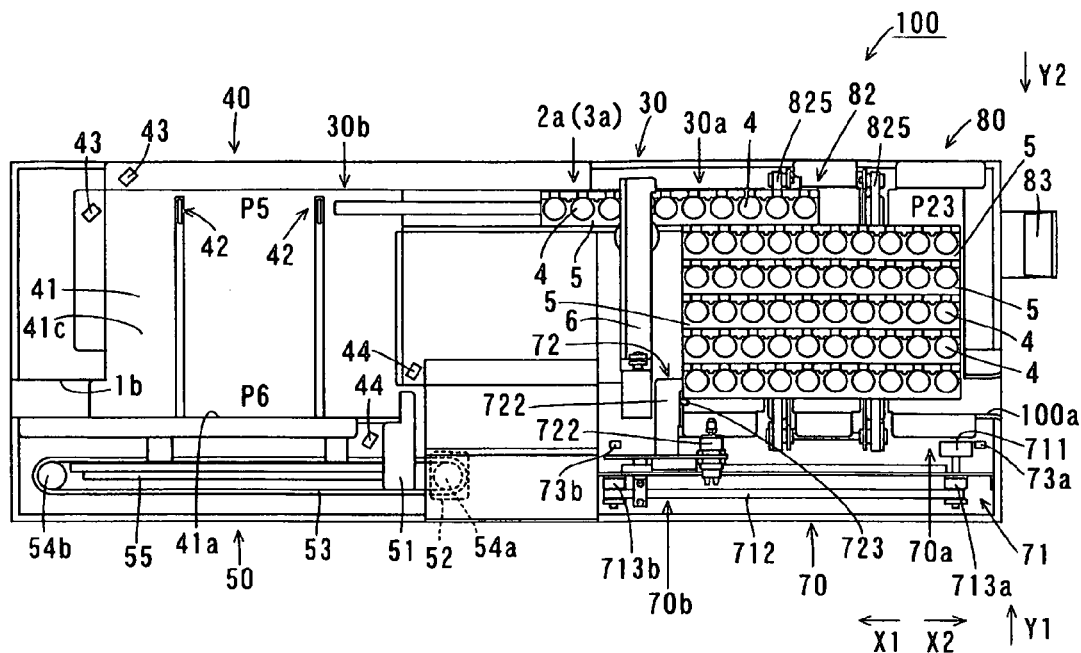
[Fig. 48]
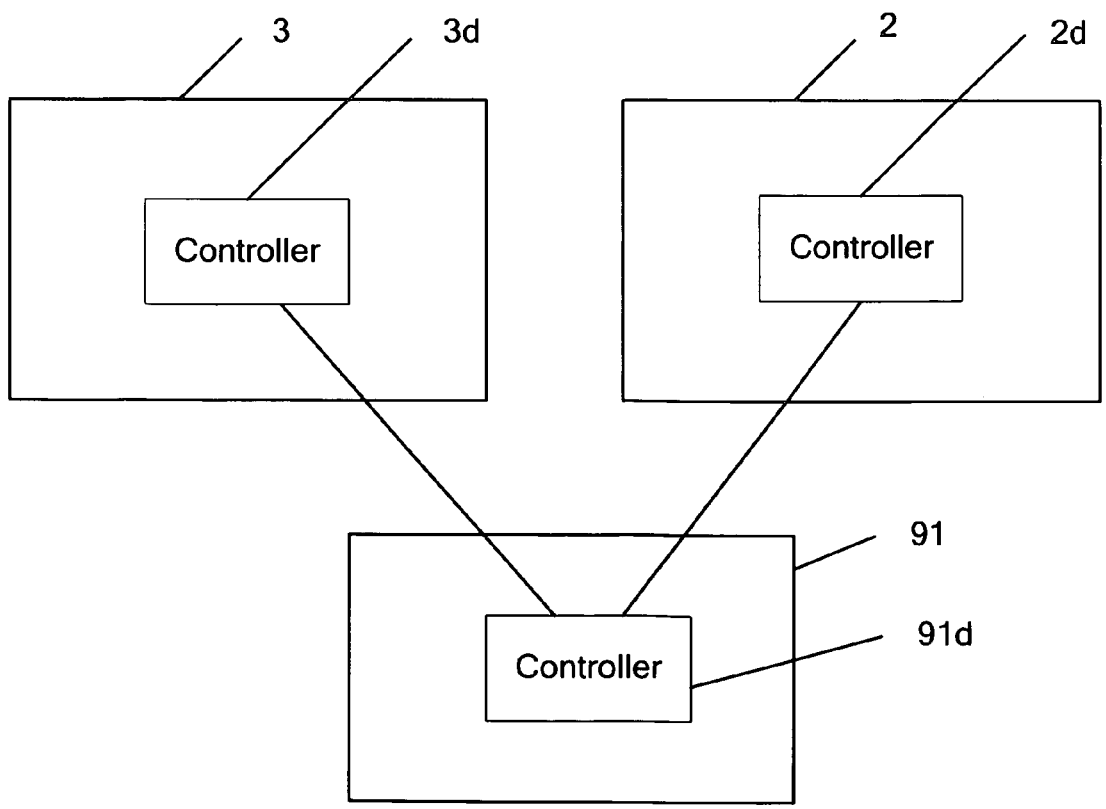

TRANSPORTING APPARATUS

FIELD OF THE INVENTION

The present invention relates to a transporting apparatus, and more particularly relates to a transporting apparatus for transporting a rack accommodating specimen containers to a specimen supplying position of a specimen processing apparatus for processing the specimen samples.

BACKGROUND

Conventional transporting apparatuses for transporting a rack accommodating sample containers to a specimen supplying position of a specimen processing apparatus for processing specimen samples are well known (for example, refer to Japanese Laid-Open Utility Model No. 63-141455). The specimen samples to be processed by the specimen processing apparatus are placed in specimen containers accommodated in a rack.

In the transporting apparatus disclosed in the previously mentioned Japanese Laid-Open Utility Model No. 63-141455, a belt is stopped when a sensor detects an edge (detection part) of identical shape provided at a predetermined pitch on a specimen frame (rack) transported by the belt, and the specimen sample in the specimen container accommodated in the rack is mixed and suctioned.

In the conventional transporting apparatus disclosed in Japanese Utility Model Filing No. 6-770, when the specimen frame (rack) is moved one pitch in a transport direction, or a direction opposite to the transport direction, it is impossible for the sensor to detect the one pitch movement of the specimen frame because the edge (detection part) on the specimen frame has identical shape. In this case, an anomaly in the transporting of the rack is not determined, and a problem arise inasmuch as the transport of the specimen frame (rack) continues, and a different specimen container than the specimen container that is supposed to be analyzed is supplied to the specimen supplying position of the specimen processing apparatus.

SUMMARY

The scope of the present invention is defined solely by the appended claims, and is not affected to any degree by the statements within this summary.

A first aspect of the transporting apparatus of the present invention provides a transporting apparatus which transports at least one specimen container accommodated in a rack to a specimen supplying position for supplying a specimen processing apparatus, comprising: a transport mechanism configured to transport the at least one specimen container to the specimen supplying position by transporting the rack; and a detection unit for obtaining information specifying the position of the rack being transported by the transport mechanism.

A second aspect of the transporting apparatus of the present invention provides a transporting apparatus which transports at least one specimen container accommodated in a rack to a specimen supplying position for supplying a specimen processing apparatus, comprising: a transport mechanism configured to transport the at least one specimen container to the specimen supplying position by transporting the rack along a transport path extending in a predetermined direction; and a detection unit for obtaining information representing the position of the rack whenever a rack is transported by the transporting mechanism; wherein the position information at adjacent positions on the transport path are mutually different information.

A third aspect of the present invention provides a transport system comprising: a transport system comprising:
- a specimen processing apparatus configured to process specimen samples in a specimen container; a transporting apparatus which transports at least one specimen container accommodated in a rack to a specimen supplying position for supplying the specimen processing apparatus, comprises, a transporting mechanism configured to transport the at least one specimen container to the specimen supplying position by transporting the rack, a detection unit configured to obtain information specifying the position of the rack transported by the transporting mechanism; and
- a control unit configured to control the operation of the transporting apparatus; wherein the control unit determines whether or not a container accommodated in a rack has been transported to the specimen supplying position based on the position specifying information of the detection unit.

BRIEF DESCRIPTION OF THE DRAWINGS

FIG. 1 is a perspective view showing the transporting apparatus of a first embodiment of the present invention connected to an analyzer;

FIG. 2 is a perspective view showing the structure of the rack transported by the transporting apparatus of the first embodiment shown in FIG. 1;

FIG. 3 is a frontal view showing the structure of the rack transported by the transporting apparatus of the first embodiment shown in FIG. 1;

FIG. 4 is a perspective view showing the structure of the transporting apparatus of the first embodiment of the present invention;

FIG. 5 is a plan view showing the structure of the transporting apparatus of the first embodiment of the present invention;

FIG. 6 is a side view showing the structures on the periphery of the retention regulating mechanism of the transporting apparatus of the first embodiment of FIGS. 4 and 5;

FIG. 7 is a plan view showing the structure of a first rack transport mechanism of the transporting apparatus of the first embodiment shown in FIGS. 4 and 5;

FIG. 8 is a side view of the first rack transport mechanism of FIG. 7;

FIG. 9 is a plan view showing the transportation of a rack by the first rack transport mechanism of FIG. 7 in a stopped state;

FIG. 10 is a side view showing the connecting member of the first rack transport mechanism of FIG. 8 engaged to the rack;

FIG. 11 is a side view showing the connecting member of the first rack transport mechanism of FIG. 8 engaged to the rack;

FIG. 12 is a side view showing the structures on the periphery of a return prevention member of the transporting apparatus of the first embodiment shown in FIGS. 4 and 5;

FIG. 13 is a side view showing the return prevention member of FIG. 12 in the rotating state;

FIG. 14 is a side view showing the structures on the periphery of the retention regulating mechanism of the transporting apparatus of the first embodiment of FIGS. 4 and 5;

FIG. 15 is a side view showing the retention regulating member of the retention regulating mechanism of FIG. 14 protruding from the installation surface of the retention plate;

FIG. 16 is a plan view showing the structure of the horizontal feeding unit of the transporting apparatus of the first embodiment shown in FIGS. 4 and 5;

FIG. 17 is a side view of the horizontal feeding unit of FIG. 16;

FIG. 18 is a side view showing the connecting member of the horizontal feeding unit of FIG. 17 engaged to the rack;

FIG. 19 is a side view showing the connecting member of the horizontal feeding unit of FIG. 17 engaged to the rack;

FIG. 20 is a schematic view illustrating the transport operation of the transporting apparatus of the first embodiment of FIGS. 4 and 5;

FIG. 21 is a schematic view illustrating the transport operation of the transporting apparatus of the first embodiment of FIGS. 4 and 5;

FIG. 22 is a schematic view illustrating the transport operation of the transporting apparatus of the first embodiment of FIGS. 4 and 5;

FIG. 23 is a schematic view illustrating the transport operation of the transporting apparatus of the first embodiment of FIGS. 4 and 5;

FIG. 24 is a schematic view illustrating the transport operation of the transporting apparatus of the first embodiment of FIGS. 4 and 5;

FIG. 25 is a schematic view illustrating the transport operation of the transporting apparatus of the first embodiment of FIGS. 4 and 5;

FIG. 26 is a schematic view illustrating the transport operation of the transporting apparatus of the first embodiment of FIGS. 4 and 5;

FIG. 27 is a schematic view illustrating the transport operation of the transporting apparatus of the first embodiment of FIGS. 4 and 5;

FIG. 28 is a schematic view illustrating the transport operation of the transporting apparatus of the first embodiment of FIGS. 4 and 5;

FIG. 29 is a schematic view illustrating the transport operation of the transporting apparatus of the first embodiment of FIGS. 4 and 5;

FIG. 30 is a schematic view illustrating the transport operation of the horizontal feeding unit of the transporting apparatus of the first embodiment of FIGS. 4 and 5;

FIG. 31 is a schematic view illustrating the transport operation of the horizontal feeding unit of the transporting apparatus of the first embodiment of FIGS. 4 and 5;

FIG. 32 is a schematic view illustrating the transport operation of the transporting apparatus of the first embodiment of FIGS. 4 and 5;

FIG. 33 is a schematic view illustrating the transport operation of the transporting apparatus of the first embodiment of FIGS. 4 and 5;

FIG. 34 is a schematic view illustrating the transport operation of the transporting apparatus of the first embodiment of FIGS. 4 and 5;

FIG. 35 is a schematic view illustrating the transport operation of the horizontal feeding unit of the transporting apparatus of the first embodiment of FIGS. 4 and 5;

FIG. 36 is a schematic view illustrating the transport operation of the horizontal feeding unit of the transporting apparatus of the first embodiment of FIGS. 4 and 5;

FIG. 37 is a schematic view illustrating the transport operation of the transporting apparatus of the first embodiment of FIGS. 4 and 5;

FIG. 38 is a schematic view illustrating the transport operation of the transporting apparatus of the first embodiment of FIGS. 4 and 5;

FIG. 39 is a schematic view illustrating the transport operation of the transporting apparatus of the first embodiment of FIGS. 4 and 5;

FIG. 40 is a plan view showing the structure of the transporting apparatus of a second embodiment of the present invention;

FIG. 41 is a plan view showing the structure of a first rack transport mechanism of the transporting apparatus of the second embodiment shown in FIG. 40;

FIG. 42 is a side view of the first rack transport mechanism of FIG. 41;

FIG. 43 is a schematic view illustrating the transport operation of the transporting apparatus of the second embodiment of the present invention;

FIG. 44 is a schematic view illustrating the transport operation of the transporting apparatus of the second embodiment of the present invention;

FIG. 45 is a schematic view illustrating the transport operation of the transporting apparatus of the second embodiment of the present invention;

FIG. 46 is a schematic view illustrating the transport operation of the transporting apparatus of the second embodiment of the present invention;

FIG. 47 is a schematic view illustrating the transport operation of the transporting apparatus of the second embodiment of the present invention; and FIG. 48 is a schematic view showing the transport controller of the first embodiment of the present invention connected to an analyzer.

DETAILED DESCRIPTION OF THE PREFERRED EMBODIMENTS

The embodiments of the present invention are described below based on the drawings.

First Embodiment

FIG. 1 is a perspective view showing the transporting apparatus of a first embodiment of the present invention connected to an analyzer. FIGS. 2 and 3 are respectively a perspective view and frontal view showing the structure of the rack transported by the transporting apparatus of the first embodiment of FIG. 1. FIG. 48 is a schematic view showing the transport controller of the first embodiment of the present invention connected to an analyzer. The overall structure, which includes a first blood analyzer 2 and a second blood analyzer 3 connected to the transporting apparatus of the first embodiment is described hereinafter with reference to FIGS. 1 through 3.

The transporting apparatus of the first embodiment is, for example, connected to a first blood analyzer 2 for performing primary analysis, and a second blood analyzer 3 for performing secondary analysis, as shown in FIG. 1. The primary analysis performed by the first blood analyzer 2 is performed on all specimen samples, and the secondary analysis performed by the second blood analyzer 3 is performed on only those specimen samples that are determined to require detailed analysis based on the results of the primary analysis.

A specimen sample is placed in a specimen container 4, and the specimen container 4 is placed in a rack 5. The rack 5 is constructed so as to accommodate ten specimen containers 4, as shown in FIGS. 2 and 3. The rack 5 has a bottom part 5a that has a length in the foreground direction that is greater than the part accommodating the specimen containers 4. Empty regions are provided on the back surface side of the rack 5, and a plurality of partitions 5b are provided in the empty regions on the back surface side of the rack 5. Furthermore, a plurality of channels 5c are provided on the side surface side of the part of the rack 5 accommodating the specimen containers 4.

As shown in FIG. 1, a transporting apparatus 1 has the function of transporting a rack 5 accommodating specimen containers 4 to the respective specimen supplying positions 2a and 3a of the first blood analyzer 2 and the second blood analyzer 3. The specimen supplying position 2a of the first blood analyzer 2 is provided with a hand member 2b, for taking the specimen container 4 from the rack 5 and mixing the specimen sample in the specimen container 4 and supplying the specimen sample into the first blood analyzer 2. The specimen supplying position 3a of the second blood analyzer 3 is also provided with a hand member 3b, for taking the specimen container 4 from the rack 5 and mixing the specimen sample in the specimen container 4 and supplying the specimen sample into the second blood analyzer 3. Barcode readers 2c and 3c for reading barcodes adhered to the specimen containers 4 are respectively provided at positions forward of the transported rack 5 at the specimen supplying position 2a of the first blood analyzer 2 and specimen supplying position 3a of the second blood analyzer 3.

Specimen container rotation devices 6 for rotating the specimen containers 4 accommodated in the rack 5 are respectively provided in the region corresponding to the position toward the viewer to which the rack 5 is transported at the specimen supplying positions 2a and 3a of the transporting apparatus 1. The reading of the barcode adhered to the specimen container 4 by the barcode readers 2c and 3c is accomplished when the specimen container rotation device 6 rotates the specimen container 4.

The two transporting apparatuses 1, which are respectively connected to the first blood analyzer 2 and second blood analyzer 3, are connected through an intermediate transporting apparatus 7. The two transporting apparatuses 1, which are respectively connected to the first blood analyzer 2 and second blood analyzer 3, have identical structures.

As shown in FIG. 48, the first blood analyzer 2 is provided with a control unit 2d, the second blood analyzer 3 is provided with a control unit 3d, and the transport controller 91 (personal computer) is provided with a control unit 91d. The control unit 91d is connected to the control unit 2d and control unit 3d, respectively, by landline or wireless connection so as to be capable of communication. The transport controller 91 is connected to the transporting apparatus 1 so as to control the operation of the transporting apparatus 1 (not shown in the drawing). The control unit 91d of the transport controller 91 determines whether or not a specimen container 4 in the rack 5 has arrived at the specimen supplying position 2a or 3a of the transporting apparatus 1 based on signals from a detection unit 34 for detecting the transport position of the rack 5 conveyed by the transporting apparatus 1 described later. The control unit 91d commands the control unit 2d or the control unit 3d so as to bring the specimen container 4 arrived at the specimen supplying position 2a or 3a of the transporting apparatus 1 to the first blood analyzer 2 or the second blood analyzer 3 when the control unit 91d determines the presence of the specimen container 4 in the rack 5 arrived at the specimen supplying position 2a or 3a of the transporting apparatus 1.

FIGS. 4 and 5 are a perspective view and plan view, respectively, showing the structure of the transporting apparatus of a first embodiment of the present invention. FIGS. 6 through 19 are detailed drawings showing the structure of the transport apparatus of the first embodiment of FIGS. 4 and 5. The structure of the transporting apparatus 1 of the first embodiment is described in detail below with reference to FIGS. 4 through 19.

The transporting apparatus 1 of the first embodiment includes an input delivery unit 10, retention unit 20, horizontal feeding unit 30, discharge unit 40, and output delivery unit 50, as shown in FIGS. 4 and 5.

The input delivery unit 10 of the transporting apparatus 1 is provided to deliver a rack 5, which has been introduced from the entrance 1a of the transporting apparatus 1, to the retention unit 20 side after being moved in the X1 direction. The input delivery unit 10 includes a rack take-in mechanism 11, and rack take-out mechanism 12.

The rack take-in mechanism 11 of the transporting apparatus 1 is provided to move a rack 5, which has been introduced from the entrance 1a, in the X1 direction. The rack take-in mechanism 11 is configured by a conveyor belt 111, pulleys 112a and 112b, motor 113, detection unit 114, and transmission-type sensor 115. The conveyor belt 111 is installed on the pulleys 112a and 112b, and the pulley 112a is linked to the motor 113. Thus, the conveyor belt 111 is driven through the pulley 112a by driving the motor 113. Accordingly, when a rack 5 is introduced from the entrance 1a, the rack 5 is moved in the X1 direction by driving the conveyor belt 111 in the X1 direction.

The detection unit 114 of the rack take-in mechanism 11 is provided to detect the arrival of a rack 5, which is being moved in the X1 direction by the conveyor belt 14, at a take-out position P1. The take-out position P1 is a position at which the rack 5 can be moved to the retention unit 20 side by the rack take-out mechanism 12. The detection unit 114 has a detection pin 114a, compression spring 114b, and transmission-type sensor 114c. A force is exerted by the compression spring 114b on one end of the detection pin 114a, such that the detection pin 114a projects to the take-out position P1 side. The transmission-type sensor 114c is disposed at the other end of the detection pin 114a. When a rack 5 is transported to the takeout position P1 by the conveyor belt 111, the projecting end of the detection pin 114a is pressed by the rack 5, such that the detection pin 114a is moved in the X1 direction against the force exerted by the compression spring 114b. Thus, since the other end of the detection pin 114a blocks the transmission-type sensor 114c, the arrival of the rack 5 being conveyed by the conveyor belt 111 in the X1 direction at the take-out position P1 can be detected.

The transmission-type sensor 115 of the rack take-in mechanism 11 is provided to detect the presence/absence of a rack 5 at the take-out position P1, and detect when a rack 5 has been taken out from the takeout position P1 to the retention unit 20 side by the rack take-out mechanism 12. The transmission-type sensor 115 is disposed so as to be blocked when a rack 5 is present at the takeout position P1.

The rack take-out mechanism 12 of the input delivery unit 10 is provided to take a rack 5, which has been transported to the take-out position P1, to the retention unit 20 side. The rack take-out mechanism 12 is configured by a takeout member 121 direct-acting guide 122, arm 123, and motor 124. The takeout member 121 is mounted on the direct-acting guide 122, and the direct-acting guide 122 is arranged so as to extend in the Y1 direction (Y2 direction). A slot 123a is formed at one end of the arm 123. This end of the arm 123 is mounted on the take-out member 121 through the slot 123a, and the other end of the arm 123 is linked to the rotating shaft of the motor 124. Thus, one end of the arm 123 is rotated by the drive of the motor 124, such that the take-out member 121 is moved in the direction (Y1 direction) of extension of the direct-acting guide 122. Accordingly, when a rack 5 is present at the take-out position P1, the rack 5 is moved to the retention unit 20 side by the take-out member 121.

The retention unit 20 of the transporting apparatus 1 is provided to retain the rack 5 that has been transported from the entrance la to the specimen supplying position 2a (3a). In the first embodiment, the retention unit 20 has the function of again retaining a rack 5, which has been moved from the specimen supplying position 2a (3a) in a direction opposite of the transport direction to repeat an analysis. The retention unit 20 includes a retention plate 21, first rack transport mechanism 22, transmission-type sensors 23 and 24, return prevention member 25, retention regulating mechanism 26, and barcode reader 27.

The retention plate 21 of the retention unit 20 has a rack contact part 21a, retention regulating unit 21b, a pair of holes 21c and a pair of holes 21d, and a notch 21e. The rack contact part 21a is provided on the retention plate on the opposite side relative to the input delivery unit 10. The rack contact part 21a is formed by bending the retention plate 21 at a right angle relative to the installation surface 21f. The region between the rack contact part 21a and the end (return prevention member 25) of the retention plate 21 on the input delivery unit 10 side is the retention region for retaining a rack 5. One part of the region the size of a rack 5 on the input delivery unit 10 side of the retention plate 21 is a rack receiving position P2 for receiving a rack 5 that has been moved from the input delivery unit 10. One part of the region the size of a rack 5 on the rack contact part 21a side of the retention plate 21 is a horizontal feed start position P3 for starting the transport of a rack 5 by the horizontal feeding unit 30.

The retention regulating unit 21b of the retention plate 21 is formed by bending a predetermined region of the rack contact part 21a parallel to the installation surface 21f. That is, the retention regulating member 21b is formed so as to project from the rack contact part 21a to the horizontal feed start position P3 in a planar view. The retention regulating member 21b is provided to prevent the rack from being placed at the horizontal feed start position P3 by an operator. Furthermore, the distance from the installation surface 21f of the retention regulating unit 21b is set so as to be less than the entire height of the rack 5, and greater than the height of the bottom part 5a of the rack 5, as shown in FIG. 6. The amount of projection of the retention regulating member 21b from the rack contact part 21a is set such that the rack 5 does not come into contact with the retention regulating member 21b when the rack 5 (bottom part 5a) abuts the rack contact part 21a.

As shown in FIGS. 4 and 5, the pair of holes 21c of the retention plate 21 are formed so as to extend from the rack receiving position P2 of the retention plate 21 to the horizontal feed starting position P3. The pair of holes 21d of the retention plate 21 are formed as rectangular slots so as to have a length in the lengthwise direction that actually matches the length of the rack 5 (bottom part 5a) in the forward direction. The pair of holes 21d of the retention plate 20 are arranged in a region separated from the rack contact part 21 by an actual distance equal to the length of the rack 5 (bottom part 5a) in the forward direction, so as to sandwich the pair of holes 21c therebetween. The region in which the pair of holes 21s are formed in the retention plate 21 is the region for regulating the retention of the rack 5 (retention regulating position P4). Furthermore, the pair of notches 21e of the retention plate 21 are formed at the end of the retention plate 21 on the input delivery unit 10 side.

In the first embodiment, the first rack transport mechanism 22 of the retention unit 20 has the function of moving a rack 5 that is retained at the installation surface 21f of the retention plate 21 from the horizontal feed start position P3 in a direction opposite to the transport direction to the rack receiving position P2 (Y2 direction), in addition to the function of moving the rack 5 retained at the installation surface 21f of the retention plate 21 from the rack receiving position P2 side to the horizontal feed start position P3 (Y1 direction). The first rack transport mechanism 22 is configured by a drive unit 22a and a rack transport unit 22b, as shown in FIGS. 7 and 8. The drive unit 22a is provided to move the rack transport unit 22b in the Y1 direction (transport direction) and Y2 direction (direction opposite the transport direction), and is disposed below the installation surface 21f of the retention plate 21. The drive unit 21a has a motor 221, intermediate belt 222, motor pulley 223, large diameter pulley 224, drive belt 225, pulleys 226a and 226b, tension pulley 227, and direct-acting guide 228. The intermediate belt 222 is installed on the motor pulley 223 and the large diameter pulley 224, and the motor pulley 223 is linked to the motor 221. The drive belt 225 is installed on the pulleys 226a and 226b, and the small diameter part 224a of the large diameter pulley 224. A tension force is exerted on the drive belt 225 by the tension pulley 227. Thus, the drive belt 225 is driven by the drive of the motor 221 at reduced speed through the intermediate belt 222, motor pulley 223 and large diameter pulley 224. The direct-acting guide 228 is disposed so as to extend in the Y1 direction (Y2 direction).

The rack transport unit 22b of the first rack transport mechanism 22 is provided to move a rack 5, which is retained at the installation surface 21f of the retention plate 21, in the Y1 direction and Y2 direction. The rack transport unit 22 includes a first moving member 229, and a second moving member 230. The first moving member 229 is linked to the drive belt 225, and the second moving member 230 is mounted on the direct-acting guide 228. The second moving member 230 has a pair of plates 230a arranged so as to be mutually opposite with a predetermined distance therebetween, and the first moving member 229 is disposed between the pair of plates 230a of the second moving member 230. The second moving member 230 is configured so as to track the movement of the first moving member 229 when the first moving member 229 is moved by the actuation of the drive belt 225.

Specifically, a shaft 231 is mounted between the pair of plates 230a of the second moving member 230, and the first moving member 229 is inserted on the shaft 231 so as to be slidably in the direction of extension of the shaft 231 (Y1 direction and Y2 direction). A compression spring 232 is installed on the shaft 231 to exert a force in the Y2 direction on the first moving member 229. Thus, when the first moving member 229 is moved in the Y1 direction by the drive belt 225 (when the first moving member 229 is moved from the position of FIG. 7 to the position of FIG. 9), the first moving member 229 presses one plate 230a of the second moving member 230 in the Y1 direction through the compression spring 232, such that the second moving member 230 is moved in the Y1 direction along the direct-acting guide 228, as shown in FIGS. 7 through 9. When the first moving member 229 is moved in the Y2 direction by the drive belt 225 (when the first moving member 229 is moved from the position of FIG. 9 to the position of FIG. 7), the first moving member 229 presses the other plate 230a of the second moving member 230 in the Y2 direction, such that the second moving member 230 is moved in the Y2 direction along the direct-acting guide 228.

As shown in FIGS. 7 and 8, a cylinder 233 and direct-acting guide 234 are mounted on the second moving member 230 of the rack transport unit 22b. The cylinder 233 is arranged so as to extend in a perpendicular direction (Z direction) relative to the installation surface 21*f* of the retention plate 21, and the direct-acting guide 234 extends in the Z direction. Furthermore, a shaft holder 235 is mounted on a cylinder rod 233*a* and direct-acting guide 234. Thus, the shaft holder 235 is moved in the direction (Z direction) of the extension of the direct-acting guide 234 by the cylinder rod 233*a* extending in the Z direction.

A shaft 236 is mounted on the shaft holder 235 of the rack transport unit 22*b*, and a pair of connectors 237*a* and a pair of connectors 237*b* are mounted on the shaft 236 so as to be pivotable on the shaft 236. One of the pair of connectors 237*a* is placed at one end of the shaft 236, and the other of the pair of connectors 237*a* is placed at the other end of the shaft 236. One of the pair of connectors 237*b* are placed at one end of the shaft 236, and the other of the pair of connectors 237*b* is placed at the other end of the shaft 236. The connectors 237*a* and 237*b* project from the installation surface 21*f* through the pair of holes 23*c* of the retention plate 21 when the shaft holder 235 is moved in the Z direction, as shown in FIGS. 10 and 11. The connectors 237*a* and 237*b* respectively have connecting surfaces 237*c* and 237*d* for engaging the interior surface of the bottom part 5*a* of the rack 5. Thus, the connectors 237*a* and 237*b* project from the installation surface 21*f*, and when the rack transport unit 22*b* is moved in the Y1 direction (Y2 direction), the rack 5 is moved in the Y1 direction (Y2 direction) by the engagement of the interior surface of the bottom part 5*a* of the rack 5 with the connecting surface 237*c* (237*d*) of the connector 237*a* (237*b*). As shown in FIG. 10, the connector 237*a* engages the interior surface of the bottom part 5*a* of the rack 5 when the rack 5 is moved in the Y1 direction, and the connector 237*b* engages the interior surface of the bottom part 5*a* of the rack 5 when the rack 5 is moved in the Y2 direction, as shown in FIG. 11.

As shown in FIGS. 10 and 11, the connector 237*a* of the rack transport unit 22*b*, receive a force exerted by the tension spring 238*a* mounted on the shaft holder 235, such that the connector 237*a* is brought into parallel with the connecting surface 237*c* and interior surface of the bottom part 5*a* of the rack 5. The connector 237*b* receives a force exerted by a tension spring 238*b* mounted on the shaft holder 235 so as to be brought into parallel with the connecting surface 237*b* and interior surface 5*a* of the rack 5. Therefore, when an external force is added from above to the connector 237*a* (237*b*), the connector 237*a* (237*b*) is rotated in a predetermined direction against the force exerted by the tension spring 238*a* (238*b*). Moreover, when the external force from above is eliminated on the connector 237*a* (237*b*), the connector 237*a* (237*b*) is rotated in the opposite direction to the predetermined direction by the force exerted by the tension spring 238*a* (238*b*) and is brought into parallel with the connecting surface 237*c* (237*d*) and the interior surface of the bottom part 5*a* of the rack 5.

As shown in FIGS. 7 and 8, a detection piece 239 is mounted on the first moving member 229 of the rack transport unit 22*b*, and a transmission-type sensor 240 is mounted on the second moving member 230. The detection piece 239 and the transmission-type sensor 230 are provided to detect a stoppage during the transport of the rack 5 in the Y1 direction by the first rack transport mechanism 22. Specifically, the detection piece 239 and transmission-type sensor 240 are arranged such that the detection piece 239 blocks the light of the transmission sensor 240 when the second moving member 230 is stationary and the first moving member 229 is moved in the Y1 direction, as shown in FIG. 9.

As shown in FIGS. 4 and 5, the transmission-type sensor 23 of the retention unit 20 is provided to detect the presence/absence of a rack 5 in the retention region outside the horizontal feed starting position P3 of the retention unit 20. The transmission-type sensor 23 is arranged so as to block the light when at least one rack 5 is retained in the retention region outside the horizontal feed starting position P3 of the retention unit 20. The transmission-type sensor 24 of the retention unit 20 is provided to detect the arrival of a rack 5, which is moved from the rack receiving position P2 side, at the horizontal feed starting position P3. The transmission-type sensor 24 is arranged so as to block the light when a rack 5 has arrived at the horizontal feed start position P3.

The return prevention member 25 of the retention unit 20 is provided to prevent a rack 5, which has been taken from the take-out position P1 and placed at the rack receiving position P2, from being returned from the rack receiving position P2 to the take-out position P1. The return preventing member 25 is disposed in a region corresponding to the notch 21*e* of the retention plate 21. The return prevention member 25 has a perpendicular surface 25*a* that is perpendicular to the installation surface 21*f* of the retention plate 21, and an inclined surface 25*b* that is inclined at a predetermined angle relative to the perpendicular surface 25*a*, as shown in FIG. 12. As shown in FIGS. 12 and 13, when a rack 5 is passing the boundary of the take-out position P1 and the rack receiving position P2, the return prevention member 25 rotates downward from the retention plate 21, and rotates upward from the retention plate 21 to return to the initial condition (condition shown in FIG. 12) when the rack 5 has passed the boundary of the take-out position P1 and the rack receiving position P2. The return prevention member 25 does not rotate relative to an external force in the Y2 direction.

As shown in FIGS. 4 and 5, the retention regulating mechanism 26 of the retention unit 20 is provided to regulate the retention of a rack 5 to the retention regulating position P4 of the retention plate 21. The retention regulating mechanism 26 is configured by a pair of retention regulating members 261, and a pair of cylinders 262, as shown in FIGS. 5 and 14. The cylinder 262 is arranged so that the cylinder rod 262*a* extends in a perpendicular direction (Z direction) relative to the installation surface 21*f* of the retention plate 21. The cylinder rod 262*a* is mounted to the surface of the retention plate 21 on the side opposite the installation surface 21*f*. Therefore, the body of the cylinder 262 moves in the Z direction toward the retention plate 21 when the cylinder rod 262*a* is extended in the Z direction, as shown in FIG. 15.

The retention regulating member 261 is mounted on the body of the cylinder 262 on the side opposite the cylinder rod 262*a*. The retention regulating member 261 is arranged so as to project from the installation surface 21*f* through the hole 21*d* of the retention plate 21 when the body of the cylinder 262 is moved in the Z direction. As shown in FIG. 5, the retention regulating member 262 is formed in a rectangular shape from a planar view, similar to the hole 21*d* of the retention plate 21, and has a length in the length direction that is substantially the same as the length of the rack 5 (bottom part 5*a*) in the forward direction. Therefore, when the retention regulating member 261 projects from the installation surface 21*f*, the retention of the rack 5 toward the retention regulating position P4 is regulated by the retention regulating member 261, as shown in FIG. 15. Moreover, when the retention regulating member 261 projects from the installation surface 21*f*, the distance between the end of the retention regulating member 261 on the horizontal feed starting position P3 side and the end of the retention plate 21 on the horizontal feed starting position P3 side is less than the length of the rack 5 (bottom part 5*a*) in the forward direction, such that the retention of the rack 5 toward the horizontal feed starting position is also regulated.

As shown in FIGS. 4 and 5, the barcode reader 27 of the retention unit 20 is provided to read the barcode of a rack 5 moving from the rack receiving position P2 side to the horizontal feed starting position P3 side.

In the first embodiment, the horizontal feeding unit 30 of the transport apparatus 1 is provided to move a rack 5, which has been transported to the horizontal feed starting position P3, to the specimen supplying position 2a (3a) and the discharge unit 40. The horizontal feeding unit 30 is configured so as to transport a rack 5 a distance of approximately 20 mm (the distance between adjacent specimen containers 4 accommodated in the rack 5). In the first embodiment, the horizontal feeding unit 30 is configured so as to move a rack 5, which has been transported to the discharge unit 40 side, in the reverse direction to the transport direction to the horizontal feed starting position P3 when performing a repeat analysis. The horizontal feeding unit 30 includes a horizontal feed plate 31, drive unit 32, rack transport unit 33, and detection unit 34, as shown in FIGS. 16 and 17.

A hole 31b extending from the horizontal feed starting position P3 to a discharge starting position P5 described later is formed in the transport surface 31a of the horizontal feed plate 31 of the horizontal feeding unit 30.

As shown in FIGS. 16 and 17, the drive unit 32 of the horizontal feeding unit 30 is provided to move the rack transport unit 33 in the X1 direction (transport direction) and X2 direction (direction opposite of the transport direction), and is disposed below the transport surface 31a of the horizontal feed plate 31. The drive unit 32 is configured by a motor 321, drive belt 322, pulleys 323a and 323b, and a direct-acting guide 324. The motor 321 is linked to the pulley 323a, and the drive belt 322 is installed on the pulleys 323a and 323b. Thus, the drive belt 322 is driven by the actuation of the motor 321 through the pulley 323a. The direct-acting guide 324 is arranged so as to extend in the X1 direction (X2 direction).

In the first embodiment, the rack transport unit 33 of the horizontal feeding unit 30 has the function of moving the rack 5 from the discharge starting position P5 to the horizontal feed starting position P3 (X2 direction) in addition to the function of moving the rack 5 on the transport surface 31a of the horizontal feed plate 31 from the horizontal feed starting position P3 to the discharge starting position P5 (X1 direction), as shown in FIGS. 4 and 5. In the horizontal feeding unit 30, the initial position 30a in FIG. 5 is a position where the horizontal feeding of the rack 5 begins by the rack transport unit 33, and the horizontal feed ending position 30b in FIG. 5 is the position where the horizontal feeding of the rack 5 ends by the rack transport unit 33. The rack transport unit 33 is configured by a moving member 331, solenoid 332, direct-acting guide 333, connector 334, and transmission-type sensor 335, as shown in FIGS. 16 and 17. The moving member 331 is mounted on the direct-acting guide 324 and is linked to the drive belt 322. Thus, the moving member 331 is moved in the direction of the extension of the direct-acting guide 324 (X1 direction and X2 direction) by the actuation of the drive belt 322. The solenoid 332 is mounted on the moving member 331, and is arranged such that the rod 332a of the solenoid 332 extends in a direction (Z direction) perpendicular to the transport surface 31a of the horizontal feed plate 31. The direct-acting guide 333 is mounted on the moving member 331, and extends in the Z direction. The connector 334 is mounted on the direct-acting guide 333 and the rod 322a of the solenoid 322. Thus, the connector 334 moves in the direction of extension (Z direction) of the direct-acting guide 333 when the rod 322a of the solenoid 322 is extended in the Z direction.

In the first embodiment, a first connector 334a and second connector 334b are integratedly provided as a unit on the connector 334 of the rack transport unit 33. The first connector 334a and the second connector 334b are disposed so as to project from the transport surface 31a through the holes 31b of the horizontal feed plate 31 when the connector 334 is moved in the Z direction, as shown in FIGS. 18 and 19. Thus, as shown in FIG. 18, the first connector 334a and the second connector 334b project from the transport surface 31a, and when the rack transport unit 33 is moved in the X1 direction, the rack 5 is moved in the X1 direction by the engagement of the interior surface of the rack 5 on the first specimen container 4 side to the first connector 334a. As shown in FIG. 19, the plate 5b of the rack 5 on the tenth specimen container 4 side engages the second connector 334b, and two racks 5 are simultaneously moved in series in the X1 direction by the engagement of the interior surface of the rack 5 on the first specimen container 4 side to the first connector 334a. FIGS. 18 and 19 show racks 5 being moved in the X1 direction. That is, in FIG. 18, the first connector 334a engages the plate 5b of the rack 5 on the first specimen container 4 side when the rack 5 is moved in the X2 direction. Furthermore, in FIG. 19, the second connector 334b engages the rack 5 on the tenth specimen container 4 side when the rack 5 is moved in the X2 direction and the first connector 334a engages the plate 5b of the rack 5 on the first specimen container 4 side.

As shown in FIGS. 16 and 17, the transmission-type sensor 335 of the rack transport unit 33 is provided to detect the projection of the first connector 334a and the second connector 334b from the transport surface 31a of the horizontal feed plate 31. The transmission-type sensor 335 is arranged such that the light is blocked by the detection piece 334c mounted on the connector 334 when the first connector 334a and the second connector 334b project from the transport surface 31a of the horizontal feed plate 31.

The detection unit 34 of the horizontal feeding unit 30 is provided to detect the position of the rack transport unit moving in the X1 direction and X2 direction. The detection unit 34 is configured by transmission-type sensors 341a and 341b, and a detection panel 343. The transmission-type sensor 341a is provided to detect a rack transport unit 33 that has been moved to the initial position 30a (refer to FIG. 5). The transmission-type sensor 341a is arranged such that the light is blocked by the detection piece 331a of the moving member 331 of the rack transport unit 33 when the rack transport unit 33 has been moved to the initial position 30a. The transmission-type sensor 341b is provided to detect a rack transport unit 33 that has been moved to horizontal feed end position 30b (refer to FIG. 5). The transmission-type sensor 341b is arranged such that light is blocked by a detection piece (not shown in the drawing) of the moving member 331 of the rack transport unit 33 when the rack transport unit 33 has been moved to the horizontal feed end position 30b.

In the first embodiment, the transmission-type sensors 342a and 342b of the detection unit 34 are provided to detect the transport position of the rack 5. The transmission-type sensors 342a and 342b are mounted on the moving member 331 of the rack moving member 33. The light-emitting unit and light-receiving unit of the transmission-type sensors 342a and 342b are arranged so as to confront one another with the detection panel 343 disposed therebetween. The transmission-type sensors 342a and 342b are disposed so as to be separated by a predetermined distance in the movement direction (X1 direction and X2 direction) of the rack transport unit 33. In the first embodiment, the detection panel 343 of the detection unit 34 has a plurality of square-shape detection holes 343a through 343h arrayed in the movement direction (X1 direction and X2 direction) of the rack transport unit 33.

The detection holes 343a through 343h are provided to change the transmission-type sensors 342a and 342b to the transmit (ON) state or block (OFF) state. The detection holes 343a through 343h are further arranged to change the state of at least one of the transmission-type sensors 342a and 342b (ON state and OFF state) whenever the rack transport unit 33 is moved one pitch in the X1 direction as the rack transport movement 33 is moved at the approximate 20 mm pitch in the X1 position. Thus, the combinations of the ON state and OFF state of the transmission-type sensors 342a and 342b is changed each time the rack transport unit 33 is moved one pitch in the X1 direction. That is, the position of the rack transport unit 33 is detected by the combination of ON state and OFF state of the transmission-type sensors 342a and 342b.

When the transmission-type sensor 342a is positioned in the region corresponding to the detection hole 343a in the detection unit 34, the rack transport unit 33 is moved to the initial position 30a (refer to FIG. 5). When the transmission-type sensor 342a is position in the region corresponding to the detection hole 343g, the rack transport unit 33 is moved to the horizontal feed ending position 30b (refer to FIG. 5). The detection holes 343a through 343g are arranged sequentially in the X1 direction (from the initial position 30a to the horizontal feed ending position 30b). The detection hole 343h is separated by a predetermined distance in the X2 direction from the detection hole 343a.

As shown in FIGS. 4 and 5, the discharge unit 40 of the transporting apparatus 1 is provided to transport the a rack 5, which has been moved from the horizontal feeding unit 30 to the discharge unit 490, to a position from which the rack 5 can be delivered from an output opening 1b by a transport unit 50. The discharge unit 40 includes a discharge plate 41, second rack transport mechanism 42, and transmission-type sensors 43 and 44.

The discharge plate 41 of the discharge unit 40 has a rack contact part 41a, and a pair of holes 41b. A region of the size of a single rack 5 on the horizontal feeding unit 30 side of the discharge plate 41 is the discharge starting position P5 for starting the transport of a rack 5 in the discharge unit 40. A region of the size of a single rack 5 on the side of the discharge plate 41 opposite the discharge starting position P5 is output starting position P6 for starting the transport of a rack 5 from the output opening 1b by the transport unit 50. The rack contact part 41a is provided on the output starting position P6 side of the discharge plate 41. The rack contact part 41a is formed by bending the discharge plate 41 in a direction perpendicular to the discharge surface 41c. The pair of holes 41b of the discharge plate 41 are formed in the discharge plate 41 and extend from the discharge starting position P5 to the output starting position P6.

A second rack transport mechanism 42 of the discharge unit 40 is provided to move a rack 5 on the discharge surface 41c of the discharge plate 41 in the Y2 direction, and is provided below the discharge surface 41c of the discharge plate 41. The second rack transport mechanism 42 has a pair of connectors 421 that engage the interior surface of the bottom part 5a of the rack 5 when the rack 5 is moved in the Y2 direction. The connectors 421 are disposed in a region corresponding to the holes 41b of the discharge plate 41, and are movable in the Y2 direction (Y1 direction) in the holes 41b by the drive unit of the rack transport mechanism 42 not shown in the drawing. The connectors 421 are configured so as to project from the discharge surface 41c through the holes 41b of the discharge plate 41 when the rack 5 is moved in the Y2 direction.

The transmission-type sensor 43 of the discharge unit 40 is provided to detect the arrival of a rack 5, which is moving from the horizontal feeding unit 30 in the X1 direction, at the discharge starting position P5. The transmission-type sensor 43 is disposed such that the light is blocked when the rack 5 arrives at the discharge starting position P5. The transmission-type sensor 44 of the discharge unit 40 is provided to detect the arrival of a rack 5, which is moving from the discharge starting position P5 in the Y2 direction, at the output starting position P6. The transmission-type sensor 44 is disposed such that the light is blocked when the rack 5 arrives at the output starting position P6.

The output delivery unit 50 is provided to transport a rack 5, which has been moved to the output starting position P6 in the discharge unit 40, from the output opening 1b. The output delivery unit 50 includes a rack transport member 51, motor 52, drive belt 53, pulleys 54a and 54b, and direct-acting guide 55.

The rack transport member 51 of the output delivery unit 50 is provided to transport a rack 5, which has been moved to the output starting position P6, in the X1 direction (output opening 1b side). The motor 52 is linked to the pulley 54a, and the drive belt 53 is installed on the pulleys 54a and 54b. Thus, the drive belt 53 is driven by the actuation of the motor 52 through the pulley 54a. The direct-acting guide 55 is arranged so as to extend in the X1 direction (X2 direction). The rack transport member 51 is linked to the drive belt 53, and mounted on the direct-acting guide 55. Thus, the rack transport member 51 is moved in the direction of extension of the direct-acting guide 55 (X1 direction and X2 direction) by the actuation of the drive belt 53.

The transport operation of the transporting apparatus 1 of the first embodiment is described below with reference to FIGS. 1, 5, 9, and 20 through 39.

First, a first rack 5 is introduced through the entrance opening la to the input delivery unit 10 of the transporting apparatus 1, as shown in FIG. 20. At this time in the input delivery unit 10, the conveyor belt 111 of the rack transport mechanism 11 is actuated. Thus, rack 5 is moved from the entrance opening la to the take-out position P1 (refer to FIG. 5) by the conveyor belt 111. Then, the arrival of the first rack 5 at the take-out position P1 is detected by the detection unit 114. The presence of the first rack 5 at the take-out position P1 is detected by the transmission-type sensor 115.

As shown in FIG. 21, in the input delivery unit 10, the take-out member 121 of the rack take-out mechanism 12 is moved in the Y1 direction after the first rack 5 has arrived at the take-out position P1. Thus, the first rack 5 is moved from the takeout position P1 to the rack receiving position P2 (refer to FIG. 5). Then, the move of the first rack 5 from the take-out position P1 to the rack receiving position P2 is detected by the transmission-type sensor 115. Furthermore, the presence of the first rack 5 at the rack receiving position P2 (retention region outside the horizontal feed starting position P3 of the retention unit 20) is detected by the transmission-type sensor 23 of the retention unit 20.

Thereafter, in the retention unit 20, the first rack 5, which has arrived at the rack receiving position P2, is moved in the Y1 direction by the connector 237a (refer to FIG. 5) of the first rack transport mechanism 22, as shown in FIG. 22. Then, the retention regulating member 261 of the retention regulating mechanism 26 is housed below the installation surface 21f of the retention plate 21.

Thus, the first rack 5, which has been moved in the Y1 direction by the connector 237a (refer to FIG. 5) of the first rack transport mechanism 22, is not prevented from moving in the Y1 direction by the retention regulating member 261, and is transported to the horizontal feed starting position P3 (refer to FIG. 5), as shown in FIG. 23. Then, the arrival of the first rack 5 at the horizontal feed starting position P3 is detected by the transmission-type sensor 24.

In the retention unit 20, when the first rack 5 arrives at the horizontal feed starting position P3 (refer to FIG. 5), the movement of the first rack 5 in the Y1 direction is stopped when the first rack 5 abuts the rack contact part 21a of the retention plate 21. The operation of the rack transport unit 22b of the first rack transport mechanism 22 at this time is described below, as shown in FIG. 9. The drive belt 225, which is driven by the actuation of the motor 221, is linked to the first moving member 229 of the rack transport unit 22, and since the connector 237a for engaging the first rack 5 is not mounted, the movement of the first moving member 229 in the Y1 direction continues while the motor 221 is actuated. Since the drive belt 225 is not linked to the second moving member 230 of the rack transport unit 22b, and the connector 237a for engaging the first rack 5 is mounted through various parts, the movement of the second moving member 230 in the Y1 direction is stopped. Thus, since only the first moving member 229 moves in the Y1 direction against the force exerted by the compression spring 232, the transmission-type sensor 240 mounted on the second moving member 230 is blocked by the detection piece mounted on the first moving member 229. As a result, the movement of the first rack 5 to the horizontal feed starting position P3 by the first rack transport mechanism 22 is stopped.

Thereafter, as shown in FIG. 24, the specimen containers 4 accommodated in the first rack 5 are sequentially moved to the specimen supplying position 2a (3a) when the horizontal feeding unit 30 moves the first rack 5 at the horizontal feed starting position P3 a pitch of approximately 20 mm in the X1 direction. The second through fourth racks 5 are transported to the retention region of the retention unit 20 in the same manner as the first rack 5. Then, in the retention unit 20, the retention regulating member 261 of the retention regulating mechanism 26 is projected from the installation surface 21f of the retention plate 21. Thus, the transport of the second and subsequent racks 5 to the retention regulating position P4 is controlled by the retention regulating member 261.

Then, when the first rack 5 has been completely moved from the horizontal fed starting position P3 in the retention unit 20, the retention regulating member 261 (refer to FIG. 5) of the retention regulating mechanism 26 is housed below the installation surface 21f of the retention plate 21, as shown in FIG. 25. Then, with the retention regulating member 261 housed below the installation surface 21f of the retention plate 21, the second through fourth racks 5 are moved in the Y1 direction by the connector 237a (refer to FIG. 5) of the first rack transport mechanism 22. Then, the second through fourth racks 5 are moved in the Y1 direction until the second rack 5 is moved to the horizontal feed starting position P3 (refer to FIG. 5).

Thereafter, in the retention unit 20, the third and fourth racks 5 are moved in the Y2 direction, that is, the direction opposite the transport direction, by the connector 237b (refer to FIG. 5) of the first rack transport mechanism 22, as shown in FIG. 26. Then, the third and fourth racks 5 are moved in the Y2 direction until the third rack 3 is moved to the retention region adjacent to the retention regulating position P4. Thereafter, the retention regulating member 261 of the retention regulating mechanism 26 projects from the installation surface 21f of the retention plate 21.

The operation when it is determined that repeat analysis is required for a specimen sample in a specimen container 4 accommodated in the first rack 5 in the state shown in FIG. 26 is described below.

When it is determined that repeat analysis is required for a specimen sample in a specimen container 4 accommodated in the first rack 5, first, in the retention unit 20, the retention regulating member 261 (refer to FIG. 5) of the retention regulating mechanism 26 is housed below the installation surface 21f of the retention plate 21. Thereafter, with the retention regulating member 261 housed below the installation surface 21f of the retention plate 21, the second rack 5 is moved to the retention regulating position P4 (refer to FIG. 5) by the connector 237b (refer to FIG. 5) of the first rack transport mechanism 22.

Then, as shown in FIG. 28, the first rack 5 is moved to the horizontal feed starting position P3 (refer to FIG. 5) when the first rack 5 is transported in the X2 direction (direction opposite the transport direction) by the horizontal feeding unit 30. Thereafter, as shown in FIG. 29, the first rack 5 is again moved to the specimen supplying position 2a (3a) when the horizontal feeding unit 30 again moves the first rack 5 at the horizontal feed starting position P3 a pitch of approximately 20 mm in the X1 direction.

After the first rack 5 has been completely moved to the horizontal feed starting position, the second rack 5 is transported to the horizontal feed starting position P3 by the connector 237a (refer to FIG. 5) of the first rack transport mechanism 22, so as to be returned to the condition prior to the repeat analysis condition (refer to FIG. 26).

The transport operation performed by the horizontal feeding unit 30 is described in detail below.

First, in the initial state shown in FIG. 30, the rack transport unit 33 of the horizontal feeding unit 30 is moved to the initial position 30a. When the rack transport unit 33 has been moved a pitch of approximately 20 mm in the X1 direction, the transmission-type sensors 342a and 342b of the rack transport unit 33 operate as described below.

As shown in FIG. 30, when the rack transport unit 33 is moved to the initial position 30a, the transmission-type sensor 342a is set to the transmission (ON) state, and the transmission-type sensor 342b is set to the blocked (OFF) state. As shown in FIG. 31, when the rack transport unit 33 is moved only approximately 20 mm (one pitch) from the initial position 30a, the rack transport unit 33 is transported to the first transport position 30c at which the transmission-type sensor 342a is set to the OFF state, and the transmission-type sensor 342b is set to the ON state. As shown in FIG. 32, when the rack transport unit 33 is moved only approximately 40 mm (two pitches) from the initial position 30a, the rack transport unit 33 is transported to the second transport position 30d at which the transmission-type sensor 342a is set to the ON state, and the transmission-type sensor 342b is set to the OFF state. As shown in FIG. 33, when the rack transport unit 33 is moved only approximately 60 mm (three pitches) from the initial position 30a, the rack transport unit 33 is transported to the third transport position 30e at which the transmission-type sensor 342a and the transmission-type sensor 342b are both set to the ON state. In the first embodiment, the rack 5 is transported by the horizontal feeding unit 30 to any among the first transport position 30c at which the transmission-type sensor 342a is set to the blocked (OFF) state and the transmission-type sensor 342b is set to the transmission (ON) state; second transport position 30d at which the transmission-type sensor 342a is set to the transmission (ON) state and the transmission-type sensor 342b is set to the blocked (OFF) state; and third transport position 30e at which the transmission-type sensor 342a and the transmission-type sensor 342b are both set to the transmission (ON) state. The first transport position 30c, second transport position 30d, and third transport position 30e are provided so as to be sequentially adjacent in the stated order in the transport direction (X1 direction).

Thus, each time the rack transport unit 33 is moved one pitch in the X1 direction, the rack 5 is transported to either he first transport position 30c, second transport position 30d, or third transport position 30e, that is, the rack 5 is transported to a different transport position with each one pitch of movement. In this way the shift can be readily detected when the position of the rack 5 is shifted one pitch. Furthermore, since the movement of the rack 5 can be reliably detected, it is possible to specify the specimen container 4 in the rack 5 moved to the specimen supplying position.

In the horizontal feeding unit 30, the barcode adhered on the first specimen container 4 of the first rack 5 is read when the first rack 5 is moved approximately 40 mm from the initial position 30a by the rack transport unit 33 (refer to FIG. 32). As shown in FIG. 34, when the first rack 5 is moved approximately 80 mm (four pitches) from initial position 30a by the rack transport unit 33, the specimen in the first specimen container 4 of the first rack 5 is agitated by the hand member 2b (refer to FIG. 1) of the first blood analyzer 2. As shown in FIG. 35, when the first rack 5 is moved approximately 100 mm (five pitches) from initial position 30a by the rack transport unit 33, the specimen in the first specimen container 4 of the first rack 5 is supplied to the first blood analyzer 2 by the hand member 2b (3b).

When it is determined that repeat analysis is required for a specimen sample in a specimen container 4 accommodated in the first rack 5, the rack transport unit 33 is moved in the X2 direction, as shown in FIG. 36. Then, the rack transport unit 33 is moved in the X2 direction until the transmission-type sensor 342a of the rack transport unit 33 arrives at the region corresponding to the detection hole 343h. At this time the transmission-type sensors 342a and 342b are set to the ON state and OFF state, respectively.

As shown in FIG. 37, the first rack 5 is transported to the discharge starting position P5 (refer to FIG. 5) when the first rack 5 is moved approximately 20 mm (one pitch) in the X1 direction by the horizontal feeding unit 30. Then, the arrival of the first rack 5 at the discharge starting position P5 is detected by the transmission-type sensor 43 of the discharge unit 40.

Then, in the discharge unit 40, the first rack 5, which has arrived at the discharge starting position P5 (refer to FIG. 5) is moved in the Y2 direction by the connector 421 (refer to FIG. 5) of the second rack transport mechanism 42 and arrives at the take-out starting position P6, as shown in FIG. 38. Then, the arrival of the first rack 5 at the take-out starting position P6 is detected by the transmission-type sensor 44 of the discharge unit 40.

Finally, in the output delivery unit 50, after the first rack 5 is moved to the takeout starting position P6, the rack transport member 51 is move din the X1 direction, as shown in FIG. 39. Thus, the first rack 5 is moved from the output opening 1b since the first rack 5 at the take-out starting position P6 is moved in the X1 direction.

In the first embodiment described above, when the rack 5 is transported by the horizontal feeding unit 30 to either the first transport position 30c, second transport position 30d, or third transport position 30e, whether or not the rack 5 has arrived at the transport position (first transport position 30c, second transport position 30d, or third transport position 30e) can be confirmed when the transmission-type sensors 342a and 342b detect the detection holes 343athrough 343g by providing a horizontal feeding unit 30 for transporting a rack 5 to the specimen supplying position 2a and 3a of a first blood analyzer 2 or second blood analyzer 3, transmission-type sensors 342a and 342b for detecting the transport position of the rack 5, and detection holes 343a through 343g for indicating the transport positions (first transport position 30c, second transport position 30d, or third transport position 30e) detectable by the transmission-type sensors 342a and 342b. Therefore, the movement of the rack 5 can be reliably detected by the change in the detection status of the transmission-type sensors 342a and 342b even when the rack 5 is moved one pitch in either the X1 direction or X2 direction from the transport position (first transport position 30c, second transport position 30d, or third transport position 30e). Since the movement of the rack 5 can be detected in this way, it is possible to prevent supplying a specimen container 4 that is different from the specimen container 4 intended for current analysis to the first blood analyzer 2 or second blood analyzer 3.

In the first embodiment, when the rack 5 is moved one pitch (20 mm) at a time in the X1 or X2 directions between two transport positions (first transport position 30c, second transport position 30d, or third transport position 30e), the movement of the rack 5 can be readily detected by providing sequentially adjacent first transport position 30c, second transport position 30d, and third transport position 30e, and sequentially changing the detection status of the transmission-type sensor 342a and transmission-type sensor 342b among three different detection states.

In the first embodiment, in the retention unit 20, the first transport mechanism for transporting a rack 5 at the rack receiving position P2 to the horizontal feed starting position P3 is configured so as to be capable of moving the rack 5 in a direction opposite the transport direction from the horizontal feed starting position P3 toward the rack receiving position P2 side, such that a rack 5 can be moved in a direction (Y2 direction) opposite the transport direction from the horizontal feed starting position P3 toward the rack receiving position P2 side by the first rack transport mechanism 22 without intervention by an operator. Thus, when a specimen in a specimen container 4 accommodated in the first rack 5 is to be reanalyzed by the same analyzer (first blood analyzer 2 or second blood analyzer 3), the first rack 5, which has been moved from the horizontal feed starting position P3 to the specimen supplying position 2a (3a), is transported again to the horizontal feed starting position P3 and again retained in the retention unit 20; then, since the second rack 5, which was previously moved to the horizontal feed starting position by the first rack transport mechanism 22, can be moved to a region outside the horizontal feed starting position P3 of the retention unit 20 when the retained first rack 5 is again moved from the horizontal feed starting position P3 to the specimen supplying position 2a (3a), the first rack 5 is ensured of the retention region (horizontal feed starting position P3) in the retention unit 20 without the intervention of an operator. As a result, when a specimen is to be reanalyzed by the same analyzer (first blood analyzer 2 or second blood analyzer 3), the rack 5 (specimen sample) can be again transported to either the first blood analyzer 2 or the second blood analyzer 3.

In the first embodiment, the racks 5 are moved one at a time by the connectors 237a and 237b of the first rack transport mechanism 22 by configuring the first rack transport mechanism 22 so as to include the connectors 237a and 237b for engaging the rack 5. In this case, when a specimen in a specimen container 4 accommodated in the first rack 5 is to be reanalyzed by the same analyzer (first blood analyzer 2 or second blood analyzer 3), the first rack 5 can be assured of regaining the retention region (horizontal feed starting position P3) in the retention unit 20 by setting a region the size of one rack 5 adjacent to the horizontal feed starting position P3 on the rack receiving position P2 side as a region for regulating the retention of a rack 5, and moving only the second rack 5, which has already been moved to the horizontal feed starting position P3, to the region (retention regulating position P4) adjacent to the horizontal feed starting position P3 on the rack receiving position P2 side.

Second Embodiment

FIG. 40 is a plan view showing the structure of the transporting apparatus of a second embodiment of the present invention. FIGS. 41 and 42 show details of the structure of the transporting apparatus of the second embodiment of FIG. 40. The aspects of the second embodiment which differ from those of the first embodiment are described below in the case of the transport of a rack 5 by a conveyor belt 825 in a retention unit 80 with reference to FIGS. 3, and 40 through 42. The rack 5, which is moved by the transporting apparatus 100 of the second embodiment, is identical to the rack 5 shown in FIGS. 2 and 3.

The transporting apparatus 100 of the second embodiment is provided with an input delivery unit 70, retention unit 80, horizontal feeding unit 30, discharge unit 40, and output delivery unit 50, as shown in FIG. 40. The structures of the horizontal feeding unit 30, discharge unit 40, and output delivery unit 50 of the transporting apparatus 100 of the second embodiment are identical to the structures of the horizontal feeding unit 30, discharge unit 40, and output delivery unit 50 of the transporting apparatus 1 of the first embodiment.

The input delivery unit 90 of the transporting apparatus 100 is provided to transport a rack 5, which has been introduced from the entrance opening 100a of the transporting apparatus 100, in the X1 direction to the retention unit 80 side. The input delivery unit 70 includes a drive unit 71, a rack transport unit 72, and transmission-type sensors 73a and 73b.

The drive unit 71 of the input delivery unit 70 is provided to move the rack transport unit 72 in the X1 direction and X2 direction. The drive unit 71 is configured by a motor 711, drive belt 712, pulleys 713a and 713b, and a direct-acting guide 714. The motor 711 is linked to the pulley 713a, and the drive belt 712 is installed on the pulleys 713a and 713b. Thus, the drive belt 712 is driven by the actuation of the motor 711 through the pulley 713a. The direct-acting guide 714 is arranged so as to extend in the X1 direction (X2 direction).

The rack transport unit 72 of the input delivery unit 70 is provided to move a rack 5 introduced from the entrance opening 100a in the X1 direction, and functions as a retention regulating member. The input starting position 70a in FIG. 40 is the position where the rack 5 begins to be taken in by the rack transport unit 72, and the input ending position 70b in FIG. 40 is the position where the rack 5 input by the rack transport unit 72 ends. The rack transport unit 72 has a moving member 721, solenoid 722, and microswitch 723. The moving member 721 is linked to the drive belt 712, and mounted on the direct-acting guide 714. Thus, the moving member 721 is moved in the X1 direction along the direct-acting guide 714 when the drive belt 712 is driven in the X1 direction. The moving member 721 has a contact part 721a that comes into contact with a rack 5 introduced from the entrance opening 100a. The rack 5 abuts the contact part 721a of the moving member 721 and in this condition is moved in the X1 direction by the rack transport unit 72.

The microswitch 723 of the rack transport unit 72 is mounted on the contact part 721a of the moving member 721. The microswitch 723 is arranged such that the switch part of the microswitch 723 is pressed by the rack 5 when the rack 5 abuts the contact part 721a of the moving member 721. Thus, when a rack 5 abuts the contact part 721a of the moving member 721, the contact of the rack 5 with the contact part 721a is detected since the microswitch 723 is switched from the ON (OFF) state to the OFF (ON) state.

The solenoid 722 of the rack transport unit 72 is mounted on the moving member 721. The solenoid 722 is arranged such that the rod 722a of the solenoid 722 extends in the Y1 direction, and the rod 722a is inserted into a channel 5c (refer to FIG. 3) of a rack 5 abutting the contact part 721a of the moving member 721. Thus, when the rod 722a of the solenoid 722 is inserted into the channel 5c of the rack 5 and the rack transport unit 72 is moved in the X1 direction, the rack 5 is moved in the X1 direction by the engagement of the rod 722a of the solenoid 722 with the channel 5c of the rack 5.

The transmission-type sensors 73a and 73b of the input delivery unit 70 are provided to detect the position of the rack transport unit 72 moving the X1 direction and X2 direction. That is, the transmission-type sensor 73a is provided to detect the movement of the rack transport unit 72 to the input starting position. The transmission-type sensor 73a is disposed such that the light is blocked by a detection piece (not shown in the drawing) of the moving member 721 of the track transport unit 72 when the rack transport unit 72 has been moved to the input starting position 70a. The transmission-type sensor 73b is provided to detect the movement of the rack transporting unit 72 to the input ending position 70b. The transmission-type sensor 73b is disposed such that the light is blocked by a detection piece (not shown in the drawing) of the moving member 721 of the track transport unit 72 when the rack transport unit 72 has been moved to the input ending position 70b. When the rack transport unit 72 has been moved to the input starting position 70a, the moving member 721 of the rack transport unit 72 is positioned in a predetermined region above a retention plate 81 described later. When the rack transport unit 72 has been moved to the input ending position 70b, the moving member 721 of the rack transport unit 72 is position in a region separated from the retention plate 81 described later.

The retention unit 80 of the transporting apparatus 100 is provided to retain a rack 5 that has been moved from the entrance opening 100a to the specimen supplying position 2a (3a). In the second embodiment, when a repeat analysis is to be performed, the retention unit 80 has the function of retaining a rack 5 that has been moved from the specimen supplying position 2a (3a) in a direction opposite the transport direction. The retention unit 80 includes a retention plate 81, first rack transport mechanism 82, and barcode reader 83.

The retention plate 81 of the retention unit 80 has three divisions, and the three divisions of the retention plate 81 are arranged at mutually predetermined spacing. The retention plate 81 is arranged so as to have a region through which the rack transport unit 72 (contact part 721a of the moving member 721) of the rack transport unit 72 passes as it moves in the X1 direction (X2 direction). The retention plate has a rack contact part 81a. The rack contact part 81a is provided on the retention plate 81 on the opposite side from the input delivery unit 70. The rack contact part 81a is formed by bending the retention plate 81 in a direction perpendicular to the installation surface 81b. The region between the rack contact part 81a and the end of the retention plate 81 on the input delivery unit 70 side is a retention region capable of retaining a rack 5. In the retention rack 81, the region through which the rack transport unit 72 of the input delivery unit 70 passes is the rack receiving position for receiving a rack 5 transported by the input delivery unit 70. A region of the size of a single rack 5 on the rack contact part 81a side of the retention plate 81 is the horizontal feed starting position for starting the transport of a rack 5 by the horizontal feeding unit 30.

In the second embodiment, the retention of a rack 5 to the rack receiving position P22 is regulated by the moving member 721 when the rack transport unit 72 (moving member 721) of the input delivery unit 70 is moved to the input starting position 70a. That is, when the rack transport unit 72 (moving member 721) of the input delivery unit 70 is moved to the input starting position 70a, the rack transport unit 72 (moving member 721) functions as a retention regulating member to regulate the retention of the rack 5 toward the rack receiving position P22. When the rack transport unit 72 is moved to the input ending position 70b, the rack transport unit 72 (moving member 721) does not function as a retention regulating member since the rack transport unit 72 (moving member 721) is positioned in a region separated from the retention plate 81. Moreover, the transport of the rack 5 toward the rack receiving position P22 starts when the rack transport unit 72 is present in a region capable of retaining at least one rack 5 in a region outside the rack receiving position P22 of the retention unit 80.

The first rack transport mechanism 82 of the retention unit 80 has the function of moving a rack 5 in a direction (Y2 direction) opposite the transport direction from the horizontal feed starting position P23 side to the rack receiving position P22 side in addition to the function of moving a rack 5 retained on the retention plate 81 from the rack receiving position P22 side to the horizontal feed starting position P23 side (Y1 direction). The first rack transport mechanism 82 is disposed below the installation surface 81b of the retention plate 81. The first rack transport mechanism 82 is configured by a cylinder 82, direct-acting guide 822, holder 823, motor 824, two drive belts 825, a pair of pulleys 826a and a pair of pulleys 826b, a plurality of tension pulleys 827, pulley shaft 828, drive belt 829, and transmission-type sensor 830. The cylinder 821 is disposed so as to extend in a direction (Z direction) perpendicular to the installation surface 81b of the retention plate 81, and the direct-acting guide 822 is arranged so as to extend in the Z direction. The holder 823 is mounted on a cylinder rod 821a and the direct-acting guide 822. Thus, the holder 823 is moved in the direction of extension of the direct-acting guide 823 by the cylinder rod 821a extending in the Z direction.

In the first rack transport mechanism 82, the motor 824, pulley pair 826a and pulley pair 826b, and the plurality of tension springs 827 are mounted on the holder 823. The pulley pair 826a are arranged so as to mutually confront one another separated by a predetermined distance, and the pulley pair 826b are arranged so as to confront one another separated by the same distance as that separating the pulley pair 826a. The two transport belts 825 are respectively installed on the pulleys 826a and 826b on one side, and pulleys 826a and 826b on the other side. The transport belts 825 on one side and the other side are arranged so as to project from the installation surface 81b through the regions corresponding the medial areas between the three divisions of the retention plate 81 when the holder 823 is moved in the Z direction. A tension is applied by the plurality of tension springs 827 to the transport belts 825 installed on the pulleys 826a and 826b.

In the first rack transport mechanism 82, the pulley shaft 828 is linked to the pair of pulleys 826a, and the drive belt 829 is installed on the pulley shaft 828 and the rotating shaft of the motor 824. Thus, the transport belt 825 is driven by the actuation of the motor 824 through the drive belt 829, pulley shaft 828, and pulley 826a. When the transport belt 825 is driven in the Y1 direction (Y2 direction) while protruding from the installation surface 81b, the rack 5 is moved in the Y1 direction (Y2 direction) by means of the contact of the rack 5 with the driven transport belt 825.

The transmission-type sensor 830 of the first rack transport mechanism 82 is provided to detect the transport belt 825 projecting from the installation surface 81b of the retention plate 81. The transmission-type sensor 830 is disposed such that the light is blocked by a detection piece 823a mounted on the holder 823 when the transport belt 825 projects from the installation surface 81b of the retention plate 81.

FIGS. 43 through 47 are schematic views illustrating the transport operation of the transporting apparatus of the second embodiment of the present invention. The rack transport operation of the transporting apparatus 100 of the second embodiment is described below with reference to FIGS. 40, and 43 through 47.

In the retention unit 80, the first through sixth racks 5 sequentially transported from the input delivery unit 70 are moved in the Y1 direction by the transport belt 825 of the first rack transport mechanism 82, as shown in FIG. 43. Then, the first rack 5 is moved to the specimen supplying position 2a (3a) by moving the first rack 5 at the horizontal feed starting position P23 (refer to FIG. 40) approximately 20 mm (one pitch) in the X1 direction (transport direction). When the first rack 5 is moved completely from the horizontal feed starting position P23, the second through sixth racks 5 are moved in the Y1 direction by the transport belt 825 of the first rack transport mechanism 82. Then, the second through sixth racks 5 are moved in the Y1 direction until the second rack 5 reaches the horizontal feed starting position P23. Thereafter, the rack transport unit 72 of the input delivery unit 70 is moved to the input starting position 70a (X2 direction).

The operation when it is determined that repeat analysis is required for a specimen sample in a specimen container 4 accommodated in the first rack 5 in the state shown in FIG. 43 is described below.

When it is determined that repeat analysis is required for a specimen sample in a specimen container 4 accommodated in the first rack 5, first, in the input delivery unit 70, the rack transport unit 72 is moved to the input ending position 70b (X1 direction), as shown in FIG. 44. As shown in FIG. 45, the second through sixth racks 5 are
moved in the Y2 direction, that is, a direction opposite the transport direction, by the transport belt 825 of the first rack transport mechanism 82. Then, the second through sixth racks 5 are moved in the Y2 direction until the sixth rack 5 reaches the rack receiving position P22 (refer to FIG. 40).

As shown in FIG. 46, the first rack 5 is moved to the horizontal feed starting position P23 by moving the first rack 5 in the X2 direction, that is, a direction opposite the transport direction by the horizontal feeding unit 30.

Thereafter, as shown in FIG. 47, the first rack 5 is again moved to the specimen supplying position 2a (3a) by again moving the first rack 5 at the horizontal feed starting position P23 approximately 20 mm (one pitch) in the X1 direction. After the first rack 5 has been completely moved from the horizontal feed starting position P23, the second rack 5 is transported to the horizontal feed starting position P23 by the transport belt 825 of the first rack transport mechanism 82, so as to be returned to the condition prior to the repeat analysis condition (refer to FIG. 43).

The transport operations in the horizontal feeding unit 30, discharge unit 40, and output delivery unit 50 of the second embodiment are respectively identical to the transport operations of the horizontal feeding unit 30, discharge unit 40, and output delivery unit 50 of the first embodiment.

In the second embodiment, the first rack transport mechanism 82 is configured to include the transport belt 825 to move the rack 5, and all racks 5 retained in the region outside the rack receiving position P22 of the retention unit 80 can be moved simultaneously in a direction opposite the transport direction from the horizontal feed starting position P23 side to the rack receiving position P22 side by the transport belt 825 of the first rack transport mechanism 82. In this case, when a specimen in a specimen container 4 accommodated in the first rack 5 is to be reanalyzed by the same analyzer, the second rack 5, which was previously moved to the horizontal feed starting position P23, can be moved together with the third and subsequent racks 5 to a region outside the horizontal feed starting position P23 of the retention unit 80 by setting the rack receiving position P22 as a region for regulating the retention of racks 5, such that a region (horizontal feed starting position P23) for again retaining the first rack 5 in the retention unit 80 can be readily ensured.

The above disclosed embodiments are to be considered examples in all respects and in now manner limiting of the invention. The scope of the present invention is expressed in the scope of the claims and not in the description of the embodiments, and all modifications within the scope and meaning of equivalences are included within the scope of the claims.

For example, although the transporting apparatus of the present invention is connected to blood analyzers in the first and second embodiments, the present invention is not limited to this arrangement inasmuch as the transporting apparatus of the present invention may also be connected to specimen processing apparatuses other than blood analyzers.

Although the first embodiment has been described by way of example in which the transmission state and blocked state of transmission-type sensors 342a and 342b of the rack transport unit 33 are changed by providing detection holes (light transmission holes (light transmission part)) in a detection plate 343, the present invention is not limited to this arrangement inasmuch as the transmission state and blocked state of transmission-type sensors 342a and 342b of the rack transport unit 33 may be changed by providing a light blocking part capable of being detected by the sensors 342a and 342b.

Although the example of the first embodiment uses two transmission-type sensors 342a and 342b, the present invention is not limited to this arrangement inasmuch as three or more transmission-type sensors may be used. For example, when three transmission-type sensors are used, eight different patterns can be provided, excluding the pattern when all transmission-type sensors are OFF.

Although rack transport is accomplished by a first moving mechanism having connectors or transport belts in a retention unit in the first and second embodiments, the present invention is not limited to this arrangement inasmuch as the racks may be transported by a first transport mechanism other than a first transport mechanism having connectors or transport belts.

Although the first embodiment is described by way of an example in which two transmission-type sensors 342a and 342b are mounted on a moving member 33 of a rack transport unit and move together with the moving rack while the detection plate 343 is stationary, it is to be noted that the detection plate 343 may be mounted on the moving member 331 of a rack transport unit so as to move together with the moving rack while the two transmission-type sensors 342a and 342b are stationary.

What is claimed is:

1. A transporting apparatus which transports at least one specimen container accommodated in a rack to a specimen supplying position for supplying a specimen processing apparatus, comprising:
   a transport mechanism configured to transport the at least one specimen container to the specimen supplying position by transporting the rack; and
   a detection unit for obtaining information specifying the position of the rack being transported by the transport mechanism,
   wherein the detection unit comprises a position specifying member provided with markers indicating the respective positions at predetermined intervals in the transport direction; and a sensor, which is movable relative to the position specifying member, for obtaining the position specifying information by detecting the markers.

2. The transporting apparatus of claim 1, wherein
   the rack has a plurality of specimen container holding parts for respectively holding the at least one specimen container, and
   the rack position specifying information includes information of the specimen container holding part positioned at the specimen supplying position.

3. The transporting apparatus of claim 1, wherein the markers include mutually different first marker, second marker, and third marker.

4. The transporting apparatus of claim 3, wherein the first, second and third markers have mutually different combinations of a first identifier and a second identifier representing either of two types of different information.

5. The transporting apparatus of claim 3, wherein the first marker, second marker, and third marker are respectively provided in plurality, and arranged such that mutually different markers are adjacent.

6. The transporting apparatus of claim 5, wherein the first marker, second marker, and third marker are provided in this order.

7. The transporting apparatus of claim 1, wherein the position specifying member is fixedly arranged and the sensor is movable together with the rack.

8. The transporting apparatus of claim 1, wherein the sensor is fixedly arranged and the position specifying member is movable together with the rack.

9. The transporting apparatus of claim 1, wherein the sensor is a transmitting type sensor and the markers are configured by a light transmitting portion and a light blocking portion.

10. The transporting apparatus of claim 1, wherein a transporting member has an engaging part for moving the rack by engaging the rack.

11. The transporting apparatus of claim 1, wherein
    the rack position specifying information includes information of the specimen container positioned at the specimen supplying position.

12. A transporting apparatus for transporting at least one specimen container accommodated in a rack to a specimen supplying position for supplying a specimen processing apparatus, comprising:
    a transport mechanism configured to transport the at least one specimen container to the specimen supplying position by transporting the rack;
    a detection unit for obtaining information specifying the position of the rack being transported by the transport mechanism; and
    a retaining unit having a moving mechanism for receiving the rack delivered from an entrance at a first position and retaining the rack received at the first position, and transporting, in a second direction that intersects the transport direction, a rack disposed at a second position at which the transport of the rack to the specimen supplying position starts by the transporting mechanism;

wherein the moving mechanism is configured so as to be capable of moving the rack in the opposite direction of the second direction.

13. The transporting apparatus of claim 12, wherein the rack is moved by the moving mechanism such that a region exists in which the rack is not retained by the retaining unit.

14. The transporting apparatus of claim 13, wherein the moving mechanism has a engaging member for moving the rack by engaging the rack; and the region in which the rack is not retained by the retaining unit is provided adjacent to the first position side of the second position.

15. The transporting apparatus of claim 13, wherein the moving mechanism has a conveyor belt for moving the rack; and the region in which the rack is not retained by the retaining unit is the first position.

16. A transporting apparatus for transporting at least one specimen container accommodated in a rack, comprising:

a transport mechanism configured to transport the rack a predetermined distance along a transport path extending in a predetermined direction so as to transport a specimen container among a plurality of specimen containers accommodated adjacently in the rack to a specimen supplying position one by one, the predetermined distance being equal to an interval of the adjacent specimen containers accommodated in the rack; and a detection unit that obtains information specifying the specimen container which is transported to the specimen supplying position by the transport mechanism.

17. The transporting apparatus of claim 16, further comprising:

a barcode reader for reading a barcode held on the at least one specimen container, the barcode reader arranged upstream from the specimen supplying position in the predetermined direction.

18. The transporting apparatus of claim 16, wherein the detection unit comprises a position specifying member including a mark which indicates the position of the specimen container accommodated in the rack and a sensor for obtaining the information by detecting the mark.

19. A transporting apparatus for transporting at least one specimen container accommodated in a rack, comprising:

a transport mechanism configured to transport the rack by a predetermined distance along a transport path extending in a predetermined direction so as to transport a specimen container among a plurality of specimen containers held adjacently by a plurality of specimen holding parts of the rack to a specimen supplying position one by one, the predetermined distance being equal to an interval of the adjacent specimen containers accommodated in the rack; and a detection unit that obtains information specifying the specimen holding part which is transported to the specimen supplying position by the transport mechanism.

20. The transporting apparatus of claim 19, wherein the detection unit comprises a position specifying member including a mark which indicates the position of the specimen holding part and a sensor for obtaining the information by detecting the mark.

* * * * *